(12) United States Patent
Hudson et al.

(10) Patent No.: US 6,498,140 B1
(45) Date of Patent: *Dec. 24, 2002

(54) USE OF ISOLATED DOMAINS OF TYPE IV COLLAGEN TO MODIFY CELL AND TISSUE INTERACTIONS

(75) Inventors: Billy G. Hudson, Lenexa; Michael P. Sarras, Jr., Kansas City, both of KS (US)

(73) Assignee: University of Kansas Medical Center, Kansas City, KS (US)

( * ) Notice: Subject to any disclaimer, the term of this patent is extended or adjusted under 35 U.S.C. 154(b) by 28 days.

This patent is subject to a terminal disclaimer.

(21) Appl. No.: 09/589,987

(22) Filed: Jun. 7, 2000

Related U.S. Application Data

(63) Continuation of application No. 09/277,665, filed on Mar. 26, 1999, which is a continuation-in-part of application No. 09/183,548, filed on Oct. 30, 1998, now abandoned, which is a continuation of application No. 08/800,965, filed on Feb. 18, 1997, now Pat. No. 5,856,184, which is a continuation of application No. 08/497,206, filed on Jun. 30, 1995, now Pat. No. 5,691,182.

(60) Provisional application No. 60/106,170, filed on Oct. 29, 1998, and provisional application No. 60/079,783, filed on Mar. 27, 1998.

(51) Int. Cl.⁷ ............................................. A01N 37/18

(52) U.S. Cl. ........................................ 514/2; 530/326

(58) Field of Search ............................ 530/326; 514/2

(56) References Cited

U.S. PATENT DOCUMENTS

| | | | |
|---|---|---|---|
| 5,021,404 A | 6/1991 | Folkman et al. |
| 5,567,609 A | 10/1996 | Sarras et al. |
| 5,691,182 A | 11/1997 | Sarras et al. |
| 5,712,291 A | 1/1998 | D'Amato |
| 5,766,591 A | 6/1998 | Brooks et al. |
| 5,837,682 A | 11/1998 | Folkman et al. |
| 5,854,205 A | 12/1998 | O'Reilly et al. |
| 5,854,221 A | 12/1998 | Cao |
| 5,856,184 A | 1/1999 | Sarras et al. |
| 6,174,861 B1 | 1/2001 | O'Reilly et al. |
| 6,277,558 B1 | 8/2001 | Hudson |

FOREIGN PATENT DOCUMENTS

| | | |
|---|---|---|
| WO | WO 95/29242 | 11/1995 |
| WO | WO 96/35774 | 11/1996 |
| WO | WO 96/41194 | 12/1996 |
| WO | WO 97/15666 | 5/1997 |
| WO | WO 98/34634 | 8/1998 |
| WO | WO 98/54218 | 12/1998 |
| WO | WO 99/45942 | 9/1999 |
| WO | WO 99/49885 | 10/1999 |
| WO | WO 99/62944 | 10/1999 |
| WO | WO 99/65940 | 12/1999 |
| WO | WO 00/05356 | 2/2000 |
| WO | WO 00/20026 | 4/2000 |
| WO | WO 00/26368 | 5/2000 |
| WO | WO 00/59532 | 10/2000 |

OTHER PUBLICATIONS

Anderson et al., (1996) *Cancer Res.*, vol. 56, pp. 715–718.
Ausprunk et al., (1977) *Microvascular Research*, vol. 14, pp. 53–65.
Barzanski et al., (1974) *Amer. Zool.*, vol. 14, pp. 575–581.
Bode et al., (1976) *J. Cell Sci.*, vol. 20, pp. 29–46.
Brooks et al., (1994) *Science*, vol. 264, pp. 569–571.
Brooks et al., (1997) *J. Clin. Invest.*, vol. 99, pp. 1390–1398.
Brooks et al., (1998) *Cell*, vol. 92, pp. 391–400.
Butkowski et al., (1985) *J. Biol. Chem.*, vol. 260, pp. 3739–3747.
Butkowski et al., (1987) *J. Biol. Chem.*, vol. 262, pp. 7874–7877.
Butkowski et al., (1990) *J. Lab. Clin. Med.*, vol. 115, pp. 365–373.
Carter, (1984) *J. Cell Biol.*, vol. 99, pp. 105–114.
Damsky et al., (1991) *Curr. Opin. Cell Biol.*, vol. 3, pp. 777–778.
Dehan et al., (1996) *J. Biol. Chem.*, vol. 11, pp. 1983–1988.
Dehan et al., (1996) *Nephrol. Dial. Transp.*, vol. 11, pp. 2215–2222.
Ding et al., (1994) *Kidney Intl.*, vol. 46, pp. 1504–1506.
Dvorak et al., (1987) *Lab. Invest.*, vol. 57, pp. 673–686.
Field et al., (1988) *Science*, vol. 239, pp. 748–752.
Folkman, (1985) *Perspectives in Biol. and Med.*, vol. 29, pp. 10–36.
Fukada et al., (1997) *Biochem. Biophys. Res. Comm.*, vol. 231, pp. 178–182.
Gierer et al., (1972) *Nature New Biol.*, vol. 239, pp. 98–101.
Guilbaud et al., (1997) *Anti–Cancer Drugs*, vol. 8, pp. 276–282.
Gunwar et al., (1990) *J. Biol. Chem.*, vol. 265, pp. 5466–5469.
Gunwar et al., (1991) *J. Biol. Chem.*, vol. 266, pp. 14088–14094.
Gunwar et al., (1998) *J. Biol. Chem.*, vol. 273, pp. 8767–8775.
Han et al., (1997) *J. Biol. Chem.*, vol. 272, pp. 20395–20401.
Hausman et al., (1971) *J. Exp. Zool.*, vol. 177, pp. 435–446.
Hudson et al., (1993) *J. Biol. Chem.*, vol. 268, pp. 26033–26036.

(List continued on next page.)

Primary Examiner—Leon B. Lankford, Jr.
(74) Attorney, Agent, or Firm—McDonnell Boehnen Hulbert & Berghoff; David S. Harper

(57) ABSTRACT

The instant invention provides methods and kits for inhibiting angiogenesis, tumor growth and metastasis, and endothelial cell interactions with the extracellular matrix, involving contacting the tumor or animal tissue with at least one isolated type IV collagen NC1 α chain monomer. In a specific embodiment of the invention, the isolated domain of type IV collagen comprises the NC1 (α1), (α2), (α3), or (α6) chain monomer, or protein constructs having substantially the same structure as the NC1 (α1), (α2), (α3), or (α6) chain monomer.

4 Claims, 28 Drawing Sheets

OTHER PUBLICATIONS

Hynes, (1987) *Cell,* vol. 48, pp. 549–554.
Hynes, (1992) *Cell,* vol. 69, pp. 11–25.
Ingber, (1990) *PNAS USA,* vol. 87, pp. 3579–3583.
Johansson et al., (1992) *J. Biol. Chem.,* vol. 267, pp. 24533–24537.
Kahsai et al., (1997) *J. Biol. Chem.,* vol. 272, pp. 17023–17032.
Kalluri et al., (1996) *J. Biol. Chem.,* vol. 271, pp. 9062–9068.
Kefalides et al., (1993) *Kidney Intl.,* vol. 43, pp. 94–100.
Kefalides et al., (1999) *Medicina,* vol. 59, p. 553.
Kleppel et al., (1986) *J. Biol. Chem.,* vol. 261, pp. 16547–16552.
Kleppel et al., (1989) *Am. J. Pathol.,* vol. 134, pp. 813–825.
Kleppel et al., (1992) *J. Biol. Chem.,* vol. 267, pp. 4137–4142.
Langeveld et al., (1988) *J. Biol. Chem.,* vol. 263, pp. 10481–10488.
Li et al., (1992) *J. of Immunology,* vol. 149, pp. 3174–3181.
Maragoudakis et al., (1993) *Kidney Intl.,* vol. 43, pp. 147–150.
Mariyama et al., (1992) *J. Biol. Chem.,* vol. 267, pp. 1253–1258.
Martin et al., (1988) *Adv. Protein Chem.,* vol. 39, pp. 1–50.
McDonald et al., (1987) *J. Biol. Chem.,* vol. 262, pp. 2957–2967.
McDonald, (1982) *J. Cell. Biol.,* vol. 92, pp. 485–492.
Nayak et al., (1991) *J. Biol. Chem.,* vol. 266, pp. 13978–13987.
Neilson et al., (1993) *J. Biol. Chem.,* vol. 268, pp. 8402–8405.
Nicosia et al., (1990) *Lab. Invest.,* vol. 63, pp. 115–122.
Nicosia et al., (1994) *Exp. Biology,* vol. 164, pp. 197–206.
Ninomiya et al., (1995) *J. Cell Biol.,* vol. 130, pp. 1219–1229.
Oberbaumer et al., (1985) *J. Biol. Chem.,* vol. 271, pp. 9062–9068.
Paku et al., (1991) *Lab. Invest.,* vol. 65, pp. 334–346.
Peczon et al., (1980) *Exp. Eye Res.,* vol. 30, pp. 155–165.
Peissel et al., (1995) *J. Clin. Invest.,* vol. 96, pp. 1948–1957.
Petitclerc et al., (2000) *J. Biol. Chem.,* vol. 275, pp. 8051–8061.
Prestayko et al., (1998) *Meeting of the American Association for cancer research New Orleans, Louisiana, USA,* Abstract #305, vol. 39, p. 45.
Rauf et al., (1996) *Virchows Arch.,* vol. 428, pp. 281–288.
Reddy et al., (1993) *Biochem. Biophys. Acta,* vol. 1157, pp. 241–251.
Ries et al., (1995) *J. Biol. Chem.,* vol. 270, pp. 23790–23794.
Sado et al., (1991) *Virchows Archiv. B Cell Pathol.,* vol. 60, pp. 345–351.
Sado et al., (1995) *Histochem. Cell Biol.,* vol. 104, pp. 267–275.
Sado et al., (1998) *Kidney Intl.,* vol. 53, pp. 664–671.
Sarras et al., (1991) *Dev. Biol.,* vol. 148, pp. 481–494.
Sarras et al., (1991) *Dev. Biol.,* vol. 148, pp. 495–500.
Sarras et al., (1993) *Dev. Biol.,* vol. 157, pp. 383–398.
Sato et al., (1992) *Dev. Biol.,* vol. 151, pp. 111–116.
Saus et al., (1988) *J. Biol. Chem.,* vol. 263, pp. 13374–13380.
Schoefl et al., (1963) *Virehous Arch. Pathol. Anat.,* vol. 337, pp. 97–141.
Seki et al., (1998) *Histochem. Cell Biol.,* vol. 110, pp. 359–366.
Setty et al., (1998) *J. Biol. Chem.,* vol. 273, pp. 12244–12249.
Shen et al., (1990) *Connective Tissue Res.,* vol. 24, pp. 289–301.
Sugihara et al., (1996) *J. Pathol.,* vol. 178, pp. 352–358.
Tagami et al., (1992) *Cell Tissue Res.,* vol. 268, pp. 225–232.
Technau et al., (1992) *Dev. Biol.,* vol. 151, pp. 117–127.
Teicher et al., (1998) *Anticancer Res.,* vol. 18, pp. 2567–2574.
Timpl et al., (1981) *Eur. J. Biochem.,* vol. 120, pp. 203–211.
Timpl et al., (1989) *Int. Rev. Exp. Pathol.,* vol. 29, pp. 1–112.
Timpl et al., (1996) *BioEssays.,* vol. 18, pp. 123–132.
Tsilibary et al., (1994) *Contrib. Nephrol.,* vol. 107, pp. 70–79.
Varner et al., (1995) *Cell Adhesion and Comm.,* vol. 3, pp. 367–374.
Weber et al., (1984) *Eur. J. Biochem.,* vol. 139, pp. 401–410.
Weber et al., (1992) *Eur. J. Clin. Invest.,* vol. 22, pp. 138–146.
Wieslander et al., (1985) *J. Biol. Chem.,* vol. 260, pp. 8564–8570.
Wood et al., (1980) *J. Ultrastruc. Res.,* vol. 70, pp. 104–117.
Zhang et al., (1990) *Diabetologia,* vol. 33, pp. 704–707.
Zhang et al., (1994) *Dev. Biol.,* vol. 164, pp. 10–23.
Zhou et al., (1996) *Contrib. Nephrol.,* vol. 117, pp. 80–104.

CONTROL

7S DOMAIN (50µg/ml)

NC1 DOMAIN (50µg/ml)

A. α1(IV)NC1

```
       900       910       920       930       940       950
        |         |         |         |         |         |
       CTGCCGCCTGCCTGCCTGCCACTGAGGGTTCCCAGCACCATGAGGGCCTGGATCTTCTTT
                                                  M   R   A   W   I   F   F 960       970       980       990       1000      1010
        |         |         |         |         |         |
       CTCCTTTGCCTGGCCGGGAGGGCTCTGGCAGCCCCACTAGCCGACTACAAGGACGACGAT
        L   L   C   L   A   G   R   A   L   A   A   P   L   A   D   Y   K   D   D   D 1020      1030      1040      1050      1060      1070
        |         |         |         |         |         |
       GACAAGCTAGCATCTGTTGATCACGGCTTCCTTGTGACCAGGCATAGTCAAACAATAGAT
        D   K   L   A   S   V   D   H   G   F   L   V   T   R   H   S   Q   T   I   D 1080      1090      1100      1110      1120      1130
        |         |         |         |         |         |
       GACCCACAGTGTCCTTCTGGGACCAAAATTCTTTACCACGGGTACTCTTTGCTCTACGTG
        D   P   Q   C   P   S   G   T   K   I   L   Y   H   G   Y   S   L   L   Y   V 1140      1150      1160      1170      1180      1190
        |         |         |         |         |         |
       CAAGGCAATGAACGGGCCCATGGCCAGGACTTGGGCACGGCCGGCAGCTGCCTGCGCAAG
        Q   G   N   E   R   A   H   G   Q   D   L   G   T   A   G   S   C   L   R   K 1200      1210      1220      1230      1240      1250
        |         |         |         |         |         |
       TTCAGCACAATGCCCTTCCTGTTCTGCAATATTAACAACGTGTGCAACTTTGCATCACGA
        F   S   T   M   P   F   L   F   C   N   I   N   N   V   C   N   F   A   S   R 1260      1270      1280      1290      1300      1310
        |         |         |         |         |         |
       AATGACTACTCGTACTGGCTGTCCACCCCTGAGCCCATGCCCATGTCAATGGCACCCATC
        N   D   Y   S   Y   W   L   S   T   P   E   P   M   P   M   S   M   A   P   I 1320      1330      1340      1350      1360      1370
        |         |         |         |         |         |
       ACGGGGGAAAACATAAGACCATTTATTAGTAGGTGTGCTGTGTGTGAGGCGCCTGCCATG
        T   G   E   N   I   R   P   F   I   S   R   C   A   V   C   E   A   P   A   M 1380      1390      1400      1410      1420      1430
        |         |         |         |         |         |
       GTGATGGCCGTGCACAGCCAGACCATTCAGATCCCACCGTGCCCCAGCGGGTGGTCCTCG
        V   M   A   V   H   S   Q   T   I   Q   I   P   P   C   P   S   G   W   S   S 1440      1450      1460      1470      1480      1490
        |         |         |         |         |         |
       CTGTGGATCGGCTACTCTTTTGTGATGCACACCAGCGCTGGTGCAGAAGGCTCTGGCCAA
        L   W   I   G   Y   S   F   V   M   H   T   S   A   G   A   E   G   S   G   Q 1500      1510      1520      1530      1540      1550
        |         |         |         |         |         |
       GCCCTGGCGTCCCCCGGCTCCTGCCTGGAGGAGTTTAGAAGTGCGCCATTCATCGAGTGT
```

FIG. 17a

```
            A   L   A   S   P   G   S   C   L   E   E   F   R   S   A   P   F   I   E   C
     1560        1570        1580        1590        1600        1610
       |           |           |           |           |           |
     CACGGCCGTGGGACCTGCAATTACTACGCAAACGCTTACAGCTTTTGGCTCGCCACCATA
       H   G   R   G   T   C   N   Y   Y   A   N   A   Y   S   F   W   L   A   T   I 1620        1630        1640        1650        1660        1670
       |           |           |           |           |           |
     GAGAGGAGCGAGATGTTCAAGAAGCCTACGCCGTCCACCTTGAAGGCAGGGGAGCTGCGC
       E   R   S   E   M   F   K   K   P   T   P   S   T   L   K   A   G   E   L   R 1680        1690        1700        1710        1720        1730
       |           |           |           |           |           |
     ACGCACGTCAGCCGCTGCCAAGTCTGTATGAGAAGAACATAATGAAGCCTGACTCAGCTA
       T   H   V   S   R   C   Q   V   C   M   R   R   T   -   -

1740        1750        1760        1770        1780        1790
       |           |           |           |           |           |
     CCGCGGGCCCTATTCTATAGTGTCACCTAAATGCTAGAGCTCGCTGATCAGCCTCGACTG
```

```
          900       910       920       930       940       950
           |         |         |         |         |         |
          CTGCCGCCTGCCTGCCTGCCACTGAGGGTTCCCAGCACCATGAGGGCCTGGATCTTCTTT
                                                     M   R   A   W   I   F   F 960       970       980       990      1000      1010
           |         |         |         |         |         |
          CTCCTTTGCCTGGCCGGGAGGGCTCTGGCAGCCCCACTAGCCGACTACAAGGACGACGAT
           L   L   C   L   A   G   R   A   L   A   A   P   L   A   D   Y   K   D   D   D 1020      1030      1040      1050      1060      1070
           |         |         |         |         |         |
          GACAAGCTAGCCGTCAGCATCGGCTACCTCCTGGTGAAGCACAGCCAGACGGACCAGGAG
           D   K   L   A   V   S   I   G   Y   L   L   V   K   H   S   Q   T   D   Q   E 1080      1090      1100      1110      1120      1130
           |         |         |         |         |         |
          CCCATGTGCCCGGTGGGCATGAACAAACTCTGGAGTGGATACAGCCTGCTGTACTTCGAG
           P   M   C   P   V   G   M   N   K   L   W   S   G   Y   S   L   L   Y   F   E 1140      1150      1160      1170      1180      1190
           |         |         |         |         |         |
          GGCCAGGAGAAGGCGCACAACCAGGACCTGGGGCTGGCGGGCTCCTGCCTGGCGCGGTTC
           G   Q   E   K   A   H   N   Q   D   L   G   L   A   G   S   C   L   A   R   F 1200      1210      1220      1230      1240      1250
           |         |         |         |         |         |
          AGCACCATGCCCTTCCTGTACTGCAACCCTGGTGATGTCTGCTACTATGCCAGCCGGAAC
           S   T   M   P   F   L   Y   C   N   P   G   D   V   C   Y   Y   A   S   R   N 1260      1270      1280      1290      1300      1310
           |         |         |         |         |         |
          GACAAGTCCTACTGGCTCTCTACCACTGCGCCGCTGCCCATGATGCCCGTGGCCGAGGAC
           D   K   S   Y   W   L   S   T   T   A   P   L   P   M   M   P   V   A   E   D 1320      1330      1340      1350      1360      1370
           |         |         |         |         |         |
          GAGATCAAGCCCTACATCAGCCGCTGTTCTGTGTGTGAGGCCCCGGCCATCGCCATCGCG
           E   I   K   P   Y   I   S   R   C   S   V   C   E   A   P   A   I   A   I   A 1380      1390      1400      1410      1420      1430
           |         |         |         |         |         |
          GTCCACAGTCAGGATGTCTCCATCCCACACTGCCCAGCTGGGTGGCGGAGTTTGTGGATC
           V   H   S   Q   D   V   S   I   P   H   C   P   A   G   W   R   S   L   W   I 1440      1450      1460      1470      1480      1490
           |         |         |         |         |         |
          GGATATTCCTTCCTCATGCACACGGCGGCGGGAGACGAAGGCGGTGGCCAATCACTGGTG
           G   Y   S   F   L   M   H   T   A   A   G   D   E   G   G   G   Q   S   L   V 1500      1510      1520      1530      1540      1550
```

FIG. 17b

```
          |              |              |              |              |              |
          TCACCGGGCAGCTGTCTAGAGGACTTCCGCGCCACACCATTCATCGAATGCAATGGAGGC
            S  P  G  S  C  L  E  D  F  R  A  T  P  F  I  E  C  N  G  G 1560         1570         1580         1590         1600         1610
      |            |            |            |            |            |
      CGCGGCACCTGCCACTACTACGCCAACAAGTACAGCTTCTGGCTGACCACCATTCCCGAG
        R  G  T  C  H  Y  Y  A  N  K  Y  S  F  W  L  T  T  I  P  E 1620         1630         1640         1650         1660         1670
      |            |            |            |            |            |
      CAGAGCTTCCAGGGCTCGCCCTCCGCCGACACGCTCAAGGCCGGCCTCATCCGCACACAC
        Q  S  F  Q  G  S  P  S  A  D  T  L  K  A  G  L  I  R  T  H 1680         1690         1700         1710         1720         1730
      |            |            |            |            |            |
      ATCAGCCGCTGCCAGGTGTGCATGAAGAACCTGTGAGCCGGCGCGTGCCAGGGCCCTATT
         I  S  R  C  Q  V  C  M  K  N  L  -

1740         1750         1760         1770         1780         1790
      |            |            |            |            |            |
      CTATAGTGTCACCTAAATGCTAGAGCTCGCTGATCAGCCTCGACTGTGCCTTCTAGTTGC
```

FIG. 17b c. α3(IV)NC1

```
           900       910       920       930       940       950
            |         |         |         |         |         |
          CTGCCGCCTGCCTGCCTGCCACTGAGGGTTCCCAGCACCATGAGGGCCTGGATCTTCTTT
                                                     M  R  A  W  I  F  F 960       970       980       990      1000      1010
            |         |         |         |         |         |
          CTCCTTTGCCTGGCCGGGAGGGCTCTGGCAGCCCCGCTAGCCGACTACAAGGACGACGAT
           L  L  C  L  A  G  R  A  L  A  A  P  L  A  D  Y  K  D  D  D 1020      1030      1040      1050      1060      1070
            |         |         |         |         |         |
          GACAAACGTGGAGACAGTGGATCACCTGCAACCTGGACAACGAGAGGCTTTGTCTTCACC
           D  K  R  G  D  S  G  P  A  T  W  T  T  R  G  F  V  F  T 1080      1090      1100      1110      1120      1130
            |         |         |         |         |         |
          CGACACAGTCAAACCACAGCAATTCCTTCATGTCCAGAGGGGACAGTGCCACTCTACAGT
           R  H  S  Q  T  T  A  I  P  S  C  P  E  G  T  V  P  L  Y  S 1140      1150      1160      1170      1180      1190
            |         |         |         |         |         |
          GGGTTTTCTTTTCTTTTTGTACAAGGAAATCAACGAGCCCACGGACAAGACCTTGGAACT
           G  F  S  F  L  F  V  Q  G  N  Q  R  A  H  G  Q  D  L  G  T 1200      1210      1220      1230      1240      1250
            |         |         |         |         |         |
          CTTGGCAGCTGCCTGCAGCGATTTACCACAATGCCATTCTTATTCTGCAATGTCAATGAT
           L  G  S  C  L  Q  R  F  T  T  M  P  F  L  F  C  N  V  N  D 1260      1270      1280      1290      1300      1310
            |         |         |         |         |         |
          GTATGTAATTTTGCATCTCGAAATGATTATTCATACTGGCTGTCAACACCAGCTCTGATG
           V  C  N  F  A  S  R  N  D  Y  S  Y  W  L  S  T  P  A  L  M 1320      1330      1340      1350      1360      1370
            |         |         |         |         |         |
          CCAATGAACATGGCTCCCATTACTGGCAGAGCCCTTGAGCCTTATATAAGCAGATGCACT
           P  M  N  M  A  P  I  T  G  R  A  L  E  P  Y  I  S  R  C  T 1380      1390      1400      1410      1420      1430
            |         |         |         |         |         |
          GTTTGTGAAGGTCCTGCGATCGCCATAGCCGTTCACAGCCAAACCACTGACATTCCTCCA
           V  C  E  G  P  A  I  A  I  A  V  H  S  Q  T  T  D  I  P  P 1440      1450      1460      1470      1480      1490
            |         |         |         |         |         |
          TGTCCTCACGGCTGGATTTCTCTCTGGAAAGGATTTTCATTCATCATGTTCACAAGTGCA
           C  P  H  G  W  I  S  L  W  K  G  F  S  F  I  M  F  T  S  A 1500      1510      1520      1530      1540      1550
```

FIG. 17c

```
        |              |              |              |              |              |
        GGTTCTGAGGGCGCCGGGCAAGCACTGGCCTCCCCCGGCTCCTGCCTGGAAGAATTCCGA
          G  S  E  G  A  G  Q  A  L  A  S  P  G  S  C  L  E  E  F  R 1560          1570          1580          1590          1600          1610
        |              |              |              |              |              |
        GCCAGCCCATTTCTAGAATGTCATGGAAGAGGAACGTGCAACTACTATTCAAATTCCTAC
          A  S  P  F  L  E  C  H  G  R  G  T  C  N  Y  Y  S  N  S  Y 1620          1630          1640          1650          1660          1670
        |              |              |              |              |              |
        AGTTTCTGGCTGGCTTCATTAAACCCAGAAAGAATGTTCAGAAAGCCTATTCCATCAACT
          S  F  W  L  A  S  L  N  P  E  R  M  F  R  K  P  I  P  S  T 1680          1690          1700          1710          1720          1730
        |              |              |              |              |              |
        GTGAAAGCTGGGGAATTAGAAAAAATAATAAGTCGCTGTCAGGTGTGCATGAAGAAAAGA
          V  K  A  G  E  L  E  K  I  I  S  R  C  Q  V  C  M  K  K  R 1740          1750          1760          1770          1780          1790
        |              |              |              |              |              |
        CACTGAGGGCCCTATTCTATAGTGTCACCTAAATGCTAGAGCTCGCTGATCAGCCTCGAC
          H  -
```

```
      900       910       920       930       940       950
       |         |         |         |         |         |
      CTGCCGCCTGCCTGCCTGCCACTGAGGGTTCCCAGCACCATGAGGGCCTGGATCTTCTTT
                                                  M   R   A   W   I   F   F 960       970       980       990      1000      1010
       |         |         |         |         |         |
      CTCCTTTGCCTGGCCGGGAGGGCTCTGGCAGCCCCGCTAGCCGACTACAAGGACGACGAT
       L   L   C   L   A   G   R   A   L   A   A   P   L   A   D   Y   K   D   D   D 1020      1030      1040      1050      1060      1070
       |         |         |         |         |         |
      GACAAGCCTGGATACCTCGGTGGCTTCCTCCTGGTTCTCCACAGTCAGACGGACCAGGAG
       D   K   P   G   Y   L   G   G   F   L   L   V   L   H   S   Q   T   D   Q   E 1080      1090      1100      1110      1120      1130
       |         |         |         |         |         |
      CCCACCTGCCCCCTGGGCATGCCCAGGCTCTGGACTGGGTATAGTCTGTTATACCTGGAA
       P   T   C   P   L   G   M   P   R   L   W   T   G   Y   S   L   L   Y   L   E 1140      1150      1160      1170      1180      1190
       |         |         |         |         |         |
      GGGCAAGAGAAAGCTCACAATCAAGACCTTGGTCTGGCAGGGTCTTGCCTTCCCGTATTT
       G   Q   E   K   A   H   N   Q   D   L   G   L   A   G   S   C   L   P   V   F 1200      1210      1220      1230      1240      1250
       |         |         |         |         |         |
      AGCACGCTGCCCTTTGCCTACTGCAACATCCACCAGGTGTGCCACTATGCCCAGAGAAAC
       S   T   L   P   F   A   Y   C   N   I   H   Q   V   C   H   Y   A   Q   R   N 1260      1270      1280      1290      1300      1310
       |         |         |         |         |         |
      GACAGATCCTACTGGCTGGCCAGCGCTGCGCCCCTCCCCATGATGCCACTCTCTGAAGAG
       D   R   S   Y   W   L   A   S   A   A   P   L   P   M   M   P   L   S   E   E 1320      1330      1340      1350      1360      1370
       |         |         |         |         |         |
      GCGATCCGCCCCTATGTCAGCCGCTGTGCGGTATGCGAGGCCCCGGCCCAGGCGGTGGCG
       A   I   R   P   Y   V   S   R   C   A   V   C   E   A   P   A   Q   A   V   A 1380      1390      1400      1410      1420      1430
       |         |         |         |         |         |
      GTGCACAGCCAGGACCAGTCCATCCCCCCATGTCCGCAGACCTGGAGGAGCCTCTGGATC
       V   H   S   Q   D   Q   S   I   P   P   C   P   Q   T   W   R   S   L   W   I 1440      1450      1460      1470      1480      1490
       |         |         |         |         |         |
      GGGTATTCATTCCTGATGCACACAGGAGCTGGGGACCAAGGAGGAGGGCAGGCCCTTATG
       G   Y   S   F   L   M   H   T   G   A   G   D   Q   G   G   G   Q   A   L   M 1500      1510      1520      1530      1540      1550
```

FIG. 17d

```
         |           |           |           |           |           |
        TCACCTGGCAGCTGCCTGGAAGATTTCAGAGCAGCACCATTCCTTGAATGCCAGGGCCGG
         S   P   G   S   C   L   E   D   F   R   A   A   P   F   L   E   C   Q   G   R 1560        1570        1580        1590        1600        1610
    |           |           |           |           |           |
        CAGGGAACTTGCCACTTTTTCGCAAATAAGTATAGCTTCTGGCTCACAACGGTGAAAGCA
         Q   G   T   C   H   F   F   A   N   K   Y   S   F   W   L   T   T   V   K   A 1620        1630        1640        1650        1660        1670
    |           |           |           |           |           |
        GACTTGCAGTTTTCCTCTGCTCCAGCACCAGACACCTTAAAAGAAAGCCAGGCCCAACGC
         D   L   Q   F   S   S   A   P   A   P   D   T   L   K   E   S   Q   A   Q   R 1680        1690        1700        1710        1720        1730
    |           |           |           |           |           |
        CAGAAAATCAGCCGGTGCCAGGTCTGCGTGAAGTATAGCTAGGGGCCCTATTCTATAGTG
         Q   K   I   S   R   C   Q   V   C   V   K   Y   S   -

1740        1750        1760        1770        1780        1790
    |           |           |           |           |           |
        TCACCTAAATGCTAGAGCTCGCTGATCAGCCTCGACTGTGCCTTCTAGTTGCCAGCCATC
```

```
           900       910       920       930       940       950
            |         |         |         |         |         |
           CTGCCGCCTGCCTGCCTGCCACTGAGGGTTCCCAGCACCATGAGGGCCTGGATCTTCTTT
                                                    M  R  A  W  I  F  F 960       970       980       990      1000      1010
            |         |         |         |         |         |
           CTCCTTTGCCTGGCCGGGAGGGCTCTGGCAGCCCCGCTAGCTGACTACAAGGACGACGAT
            L  L  C  L  A  G  R  A  L  A  A  P  L  A  D  Y  K  D  D  D 1020      1030      1040      1050      1060      1070
            |         |         |         |         |         |
           GACAAAGGTCCCCCTGGAACCTCCTCTGTTGCACATGGATTTCTTATTACACGCCACAGC
            D  K  G  P  P  G  T  S  S  V  A  H  G  F  L  I  T  R  H  S 1080      1090      1100      1110      1120      1130
            |         |         |         |         |         |
           CAGACAACGGATGCACCACAATGCCCACAGGGAACACTTCAGGTCTATGAAGGCTTTTCT
            Q  T  T  D  A  P  Q  C  P  Q  G  T  L  Q  V  Y  E  G  F  S 1140      1150      1160      1170      1180      1190
            |         |         |         |         |         |
           CTCCTGTATGTACAAGGAAATAAAAGAGCCCACGGTCAAGACTTGGGGACGGCTGGCAGC
            L  L  Y  V  Q  G  N  K  R  A  H  G  Q  D  L  G  T  A  G  S 1200      1210      1220      1230      1240      1250
            |         |         |         |         |         |
           TGCCTTCGTCGCTTTAGTACCATGCCTTTCATGTTCTGCAACATCAATAATGTTTGCAAC
            C  L  R  R  F  S  T  M  P  F  M  F  C  N  I  N  N  V  C  N 1260      1270      1280      1290      1300      1310
            |         |         |         |         |         |
           TTTGCTTCAAGAAATGACTATTCTTACTGGCTCTCTACCCCAGAGCCCATGCCAATGAGC
            F  A  S  R  N  D  Y  S  Y  W  L  S  T  P  E  P  M  P  M  S 1320      1330      1340      1350      1360      1370
            |         |         |         |         |         |
           ATGCAACCCCTAAAGGGCCAGAGCATCCAGCCATTCATTAGTCGATGTGCAGTATGTGAA
            M  Q  P  L  K  G  Q  S  I  Q  P  F  I  S  R  C  A  V  C  E 1380      1390      1400      1410      1420      1430
            |         |         |         |         |         |
           GCTCCAGCTGTGGTGATCGCAGTTCACAGTCAGACGATCCAGATTCCCCATTGTCCTCAG
            A  P  A  V  V  I  A  V  H  S  Q  T  I  Q  I  P  H  C  P  Q 1440      1450      1460      1470      1480      1490
            |         |         |         |         |         |
           GGATGGGATTCTCTGTGGATTGGTTATTCCTTCATGATGCATACAAGTGCAGGGGCAGAA
            G  W  D  S  L  W  I  G  Y  S  F  M  M  H  T  S  A  G  A  E 1500      1510      1520      1530      1540      1550
```

FIG. 17e

```
            |          |          |          |          |          |
           GGCTCAGGTCAAGCCCTAGCCTCCCCTGGTTCCTGCTTGGAAGAGTTTCGTTCAGCTCCC
            G  S  G  Q  A  L  A  S  P  G  S  C  L  E  E  F  R  S  A  P 1560       1570       1580       1590       1600       1610
       |          |          |          |          |          |
      TTCATCGAATGTCATGGGAGGGGTACCTGTAACTACTATGCCAACTCCTACAGCTTTTGG
       F  I  E  C  H  G  R  G  T  C  N  Y  Y  A  N  S  Y  S  F  W 1620       1630       1640       1650       1660       1670
       |          |          |          |          |          |
      CTGGCAACTGTAGATGTGTCAGACATGTTCAGTAAACCTCAGTCAGAAACGCTGAAAGCA
       L  A  T  V  D  V  S  D  M  F  S  K  P  Q  S  E  T  L  K  A 1680       1690       1700       1710       1720       1730
       |          |          |          |          |          |
      GGAGACTTGAGGACACGAATTAGCCGATGTCAAGTGTGCATGAAGAGGACATAACGCGGC
       G  D  L  R  T  R  I  S  R  C  Q  V  C  M  K  R  T  -

1740       1750       1760       1770       1780       1790
       |          |          |          |          |          |
      CGCTCGAGCATGCATCTAGAGGGCCCTATTCTATAGTGTCACCTAAATGCTAGAGCTCGC
```

```
         900       910       920       930       940       950
          |         |         |         |         |         |
         CTGCCGCCTGCCTGCCTGCCACTGAGGGTTCCCAGCACCATGAGGGCCTGGATCTTCTTT
                                                    M   R   A   W   I   F   F 960       970       980       990       1000      1010
          |         |         |         |         |         |
         CTCCTTTGCCTGGCCGGGAGGGCTCTGGCAGCCCCACTAGCCGACTACAAGGACGACGAT
          L   L   C   L   A   G   R   A   L   A   A   P   L   A   D   Y   K   D   D   D 1020      1030      1040      1050      1060      1070
 |         |         |         |         |         |
GACAAGCTAGCGAGCATGAGAGTGGGCTACACGTTGGTAAAGCACAGCCAGTCGGAACAG
 D   K   L   A   S   M   R   V   G   Y   T   L   V   K   H   S   Q   S   E   Q 1080      1090      1100      1110      1120      1130
          |         |         |         |         |         |
         GTGCCCCCGTGTCCCATCGGGATGAGCCAGCTGTGGGTGGGGTACAGCTTACTGTTTGTG
          V   P   P   C   P   I   G   M   S   Q   L   W   V   G   Y   S   L   L   F   V 1140      1150      1160      1170      1180      1190
          |         |         |         |         |         |
         GAGGGGCAAGAGAAAGCCCACAACCAGGACCTGGGCTTTGCTGGCTCCTGTCTGCCCCGC
          E   G   Q   E   K   A   H   N   Q   D   L   G   F   A   G   S   C   L   P   R 1200      1210      1220      1230      1240      1250
 |         |         |         |         |         |
TTCAGCACCATGCCCTTCATCTACTGCAACATCAACGAGGTGTGCCACTATGCCAGGCGC
 F   S   T   M   P   F   I   Y   C   N   I   N   E   V   C   H   Y   A   R   R 1260      1270      1280      1290      1300      1310
 |         |         |         |         |         |
AATGATAAATCTTACTGGCTCTCCACTACCGCCCCTATCCCCATGATGCCCGTCAGCCAG
 N   D   K   S   Y   W   L   S   T   T   A   P   I   P   M   M   P   V   S   Q 1320      1330      1340      1350      1360      1370
 |         |         |         |         |         |
ACCCAGATTCCCCAGTACATCAGCCGCTGCTCTGTGTGTGAGGCACCCTCGCAAGCCATT
 T   Q   I   P   Q   Y   I   S   R   C   S   V   C   E   A   P   S   Q   A   I 1380      1390      1400      1410      1420      1430
 |         |         |         |         |         |
GCTGTGCACAGCCAGGACATCACCATCCCGCAGTGCCCCCTGGGCTGGCGCAGCCTCTGG
 A   V   H   S   Q   D   I   T   I   P   Q   C   P   L   G   W   R   S   L   W 1440      1450      1460      1470      1480      1490
 |         |         |         |         |         |
ATTGGGTACTCTTTCCTCATGCACACTGCCGCTGGTGCCGAGGGTGGAGGCCAGTCCCTG
 I   G   Y   S   F   L   M   H   T   A   A   G   A   E   G   G   G   Q   S   L 1500      1510      1520      1530      1540      1550
```

FIG. 17f

```
           |              |              |              |              |              |
     GTCTCACCTGGCTCCTGCCTAGAGGACTTTCGGGCCACTCCTTTCATCGAATGCAGTGGT
       V   S   P   G   S   C   L   E   D   F   R   A   T   P   F   I   E   C   S   G 1560          1570          1580          1590          1600          1610
      |             |             |             |             |             |
     GCCCGAGGCACCTGCCACTACTTTGCAAACAAGTACAGTTTCTGGTTGACCACAGTGGAG
       A   R   G   T   C   H   Y   F   A   N   K   Y   S   F   W   L   T   T   V   E 1620          1630          1640          1650          1660          1670
      |             |             |             |             |             |
     GAGAGGCAGCAGTTTGGGGAGTTGCCTGTGTCTGAAACGCTGAAAGCTGGGCAGCTCCAC
       E   R   Q   Q   F   G   E   L   P   V   S   E   T   L   K   A   G   Q   L   H 1680          1690          1700          1710          1720          1730
      |             |             |             |             |             |
     ACTCGAGTCAGTCGCTGCCAGGTGTGTATGAAAAGCCTGTAGGGTGGCACCTGCCACGGG
       T   R   V   S   R   C   Q   V   C   M   K   S   L   -

1740          1750          1760          1770          1780          1790
      |             |             |             |             |             |
     CCCTATTCTATAGTGTCACCTAAATGCTAGAGCTCGCTGATCAGCCTCGACTGTGCCTTC
```

FIG. 17f

USE OF ISOLATED DOMAINS OF TYPE IV COLLAGEN TO MODIFY CELL AND TISSUE INTERACTIONS

CROSS REFERENCE

The present application is a continuation of Ser. No. 09/277,665 filed Mar. 26, 1999, which is a continuation in part of U.S. patent applications Ser. No. 60/106,170 filed Oct. 29, 1998; Ser. No. 60/079,783 filed Mar. 27, 1998; and Ser. No. 09/183,548 filed Oct. 30, 1998, now abandoned which is a continuation of U.S. application Ser. No. 08/800, 965 filed Feb. 18, 1997, now U.S. Pat. No. 5,856,184, which is a continuation of U.S. application Ser. No. 08/497,206 filed Jun. 30, 1995 now U.S. Pat. No. 5,691,182, all of which are herein incorporated by reference in their entirety.

FIELD OF THE INVENTION

This invention relates to methods and kits for inhibiting angiogenesis, tumor growth and metastasis, and endothelial cell interactions with the extracellular matrix.

BACKGROUND OF THE INVENTION

Angiogenesis, the process of formation of new blood vessels, plays an important role in physiological processes such as embryonic and postnatal development as well as in wound repair. Formation of blood vessels can also be induced by pathological processes involving inflammation (e.g., diabetic retinopathy and arthritis) or neoplasia (e.g., cancer); (Folkman, 1985, Perspect, Biol. Med., 29, 10). Neovascularization is regulated by angiogenic growth factors secreted by tumor or normal cells as well as the composition of the extracellular matrix and by the activity of endothelial enzymes (Nicosia and Ottinetti, 1990, Lab. Invest., 63, 115).

During the initial stages of angiogenesis, endothelial cell sprouts appear through gaps in the basement membrane of pre-existing blood vessels (Nicosia and Ottinetti, 1990, supra; Schoefl, 1963, Virehous Arch, Pathol. Anat. 337, 97–141; Ausprunk and Folkman, 1977, Microvasc. Res. 14, 53–65; Paku and Paweletz, 1991, Lab. Invest. 63, 334–346). As new vessels form, their basement membrane undergoes complex structural and compositional changes that are believed to affect the angiogenic response (Nicosia, et. al., 1994, Exp. Biology, 164, 197–206). Early planar culture models have shown that basement membrane molecules modulate the attachment, migration and proliferation and organizational behavior of endothelial cells (Nicosia, et. al., 1994, supra). More recent studies with three-dimensional aortic culture models that more closely simulate angiogenic conditions during wound healing in vivo suggest that basement membrane is a dynamic regulator of angiogenesis whose function varies according to its molecular components (Nicosia, 1994, supra).

A common feature of all solid tumor growth is the requirement for a blood supply. Therefore, numerous laboratories have focused on developing anti-angiogenic compounds based on growth factors and their receptors. While this approach has led to some success, the number of growth factors known to play a role an angiogenesis. is large. Therefore, the possibility exists that growth factor antagonists may have only limited use in treating cancer since tumors and associated inflammatory cells likely produce a wide variety of factors that can induce angiogenesis.

In this regard, a strategy that targets a common feature of angiogenesis, such as endothelial cell adhesion to the extracellular matrix (ECM), might be expected to have a profound physiological impact on tumor growth in humans. This notion is supported by the fact that antagonists of specific ECM cell adhesion receptors such as $\alpha v\beta 3$ and $\alpha v\beta 5$ integrins can block angiogenesis. Furthermore, the $\alpha v\beta 3$ integrin is expressed most prominently on cytokine—activated endothelial and smooth muscle cells. and has been shown to be required for angiogenesis. (Varner et al., Cell Adhesion and Communication 3:367–374 (1995); Brooks et al., Science 264:569–571 (1994)). Based on these findings, a potentially powerful new approach to anti-angiogenic therapy might be to specifically target critical regulatory domains within distinct ECM components.

The basement membrane (basal lamina) is a sheet-like extracellular matrix (ECM), which is a basic component of all tissues. The basal lamina provides for the compartmentalization of tissues, and acts as a filter for substances traveling between tissue compartments. Typically the basal lamina is found closely associated with an epithelium or endothelium in all tissues of an animal including blood vessels and capillaries. The basal lamina components are secreted by cells and then self assemble to form an intricate extra-cellular network. The formation of biologically active basal lamina is important to the development and differentiation of the associated cells.

Type IV collagen has been shown to be a major structural component of basement membranes. The protomeric form of type IV collagen is formed as a heterotrimer made up from a number of different subunit chains called $\alpha 1(IV)$ through $\alpha 6(IV)$. Up to now, six genetically distinct $\alpha$-chains belonging to two classes with extensive homology have been identified, and their relative abundance has been demonstrated to be tissue specific. The type IV collagen heterotrimer is characterized by three distinct structural domains: the non-collagenous (NC1) domain at the carboxyl terminus; the triple helical collagenous domain in the middle region; and the 7S collagenous domain at the amino terminus. (Martin, et. al., 1988, Adv. Protein Chem. 39:1–50; Gunwar, et. al. 1991, J. Biol. Chem. 266:14088–14094).

The capability of expression of recombinant $\alpha(IV)$ NC1 domains provides the opportunity to study the effect of specific domains on many biological processes, such as angiogenesis, tumor metastasis, cell binding to basement membranes, and assembly of Type IV collagen molecules.

SUMMARY OF THE INVENTION

The instant invention provides methods and kits for inhibiting angiogenesis, tumor growth and metastasis, and endothelial cell interaction with the extracellular matrix, each method comprising contacting the tumor or animal tissue with an one or more isolated type IV collagen NC1 $\alpha$ chain monomer selected from the group consisting of $\alpha 1$, $\alpha 2$, $\alpha 3$, and $\alpha 6$ NC1 chain monomers.

BRIEF DESCRIPTION OF THE DRAWINGS

FIGS. 17 A–F provides the sequences of each type IV collagen a chain monomer.

DESCRIPTION OF THE PREFERRED EMBODIMENTS

Figure 1:
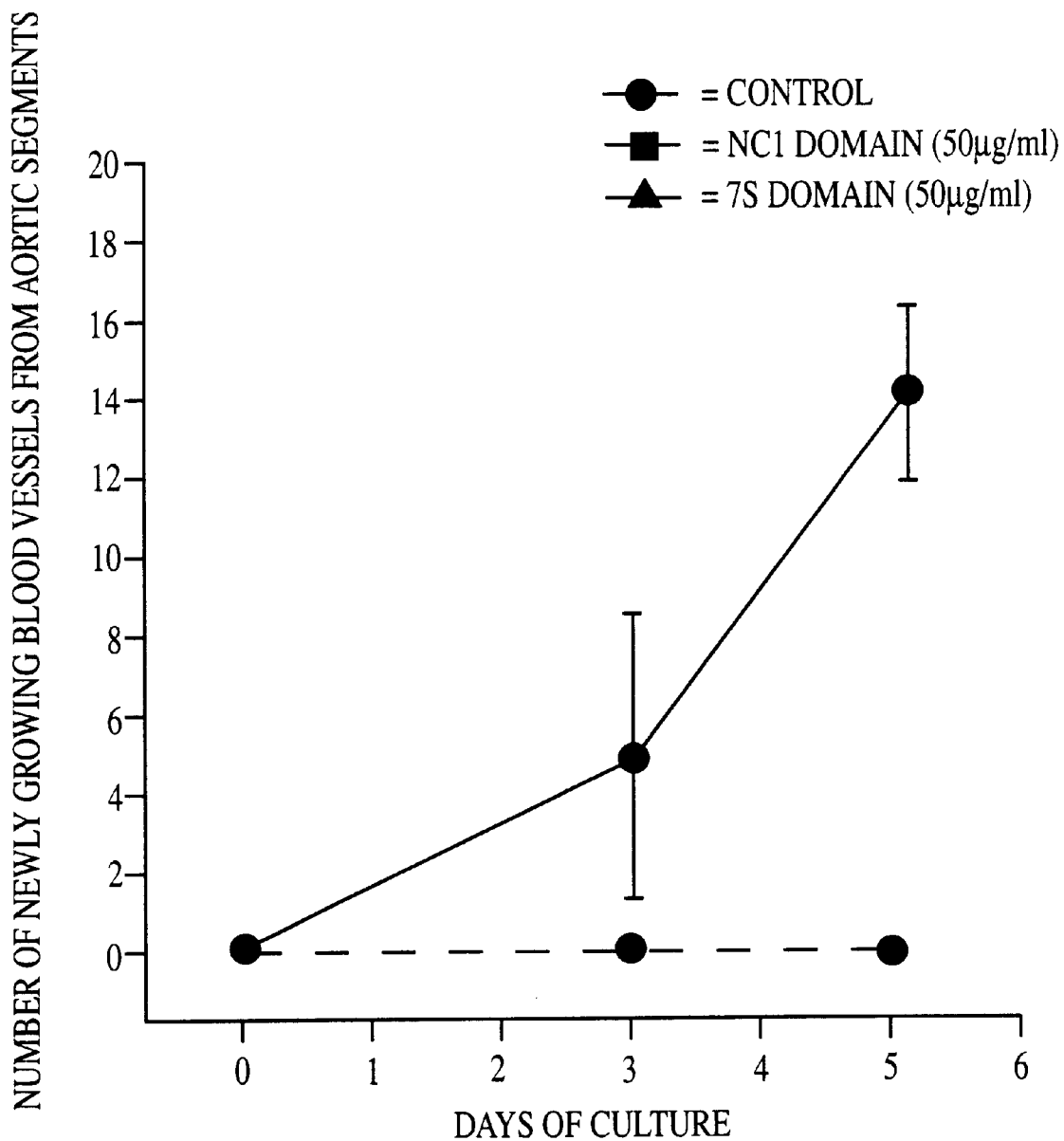
FIG. 1 illustrates the effects of NC1 (Hexamer) and 7S domains of Type IV collagen at a 50 $\mu$g/ml concentration on angiogenesis from mouse thoracic aorta organ cultures.

Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., 1990) Academic Press, Inc.); *PCR Protocols: A Guide to Methods and Applications* (Innis, et al. 1990. Academic Press, San Diego, Calif.), *Culture of Animal Cells: A Manual of Basic Technique*, 2nd Ed. (R. I. Freshney. 1987. Liss, Inc. New York, N.Y.), and *Gene Transfer and Expression Protocols*, pp. 109–128, ed. E. J. Murray, The Humana Press Inc., Clifton, N.J.).

As used herein, the term Type IV collagen domain encompasses the group of molecules including the non-collagenous NC1 domain (Hexamer) and 7S collagenous domains, as well as NC1 α chain monomers.

The invention comprises methods for using Type IV collagen NC1 α-monomers (ie: α1, α2, α3, and α6), which are defined to include such monomers isolated from any multicellular organism or produced via recombinant protein expression from a gene encoding such a monomer from any multicellular organism, and also to encompass various modifications, additions, and/or deletions to such monomers.

In one aspect, the present invention provides methods and kits for inhibiting angiogenesis in an animal tissue comprising contacting the tumor or animal tissue with an amount effective to inhibit angiogenesis of a polypeptide composition comprising one or more isolated type IV collagen NC1 α chain monomer selected from the group consisting of α1, α2, α3, and α6 NC1 chain monomers.

In another aspect, the present invention provides methods and kits for inhibiting tumor growth in tissue comprising contacting the tumor or tissue with an amount effective to inhibit tumor growth of a polypeptide composition comprising one or more isolated type IV collagen NC1 α chain monomer selected from the group consisting of α1, α2, α3, and α6 NC1 chain monomers.

In another aspect, the present invention provides methods and kits for inhibiting tumor metastasis in tissue comprising contacting the tumor or tissue with an amount effective to inhibit metastasis of a polypeptide composition comprising one or more isolated type IV collagen NC1 α chain monomer selected from the group consisting of α1, α2, α3, and α6 NC1 chain monomers.

In a further aspect, the present invention provides methods and kits for inhibiting endothelial cell interactions with the extracellular matrix in tissue comprising contacting the tumor or tissue with an amount effective to inhibit endothelial cell interactions with the extracellular matrix of a polypeptide composition comprising one or more isolated type IV collagen NC1 α chain monomer selected from the group consisting of α1, α2, α3, and α6 NC1 chain monomers.

The NC1-encoding domain of each of the six a chain cDNAs has been cloned into a vector for recombinant protein expression as previously described (Sado et al., Kidney Intl. 53:664–671 (1998), incorporated by reference herein in its entirety). The vectors are used to stably transfect human kidney 293 cells, which produce the recombinant protein. The DNA and deduced amino acid sequences of the recombinant type IV collagen alpha chain monomers produced as described are shown in FIGS. 17A–F. The first 17 amino acids corresponds to a BM40 signal sequence (which is cleaved from the mature protein), to facilitate protein secretion. All the secreted proteins (ie: mature proteins) start with the sequence APLA followed by the affinity tag, DYKDDDDK at the amino terminus. This tag facilitates purification and identification of the material, and does not interfere with biological activity of the recombinant NC1 α chain monomer.

The type IV collagen NC1 α chain monomers can be produced by any method known in the art, including using recombinant DNA technology or biochemical peptide synthesis technology, or by isolating the NC1 domains from animal sources, such as from basement membrane sources such as bovine lens capsule and bovine kidney glomeruli. (Peczon et al., Exp. Eye Res. 30:155–165 (1980); Langeveld et al., J. Biol. Chem. 263:10481–10488 (1988); Gunwar et al., J. Biol. Chem. 266:14088–14094 (1991))

In practicing the invention, the amount or dosage range of type IV collagen NC1 α chain monomers employed is one that effectively inhibits angiogenesis, tumor growth, tumor metastasis, and/or endothelial cell-extracellular matrix interactions. An inhibiting amount of NC1 α chain monomers that can be employed ranges generally between about 0.01 μg/lkg body weight and about 10 mg/kg body weight, preferably ranging between about 0.05 μg/kg and about 5 mg/kg body weight.

The NC1 α chain monomers may be administered by any suitable route, including orally, parentally, by inhalation spray, rectally, or topically in dosage unit formulations containing conventional pharmaceutically acceptable carriers, adjuvants, and vehicles. The term parenteral as used herein includes, subcutaneous, intravenous, intraarterial, intramuscular, intrastemal, intratendinous, intraspinal, intracranial, intrathoracic, infusion techniques or intraperitoneally. In preferred embodiments, the NC1 α chain monomers are administered intravenously or subcutaneously.

The NC1 α chain monomers may be made up in a solid form (including granules, powders or suppositories) or in a liquid form (e.g., solutions, suspensions, or emulsions). The NC1 α chain monomers of the invention may be applied in a variety of solutions. Suitable solutions for use in accordance with the invention are sterile, dissolve sufficient amounts of the NC1 α chain monomers, and are not harmful for the proposed application.

The NC1 α chain monomers may be subjected to conventional pharmaceutical operations such as sterilization and/or may contain conventional adjuvants, such as preservatives, stabilizers, wetting agents, emulsifiers, buffers etc.

For administration, the NC1 α chain monomers are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol, and tableted or encapsulated for conventional administration. Alternatively, the compounds of this invention may be dissolved in saline, water, polyethylene glycol, propylene glycol, carboxymethyl cellulose colloidal solutions, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The present invention may be better understood with reference to the accompanying examples that are intended for purposes of illustration only and should not be construed to limit the scope of the invention, as defined by the claims appended hereto.

EXAMPLE 1

In Vitro Effect on Angiogenesis

With modifications, the procedures of Nicosia and Ottinetti (1990), supra, and Nicosia, et. al. (1994), supra, were utilized for experiments designed to test the effect of Type IV collagen on angiogenesis under in vitro conditions. The model has been used to study the effects of growth factors and extracellular matrix molecules on the angiogenic response and employs aortic rings cultures in three-dimensional collagen gels under serum-free conditions. These experiments are outlined below.

A. Methods

Experiments were performed with 1–3 month old Swiss Webster male mice. Following anesthesia, the thoracic aorta was excised under aseptic conditions and transferred to sterile MCDB 131 sterile growth medium (Clonetics, San Diego, Calif.) containing antibiotics. Fat was dissected away from the aorta and approximately six to eight 1 mm thoracic segments were obtained from each specimen. Segments were transferred to 48 well tissue culture plates. The wells of these plates were layered with 100 microliters of Matrigel (EHS basement membrane, Collaborative Biomedical Products, Bedford, Mass.) prior to transfer of the aortic segments. The Matrigel was diluted 1:1 with MCDB 131 growth medium prior to use. The segments were centered in the wells and an additional 100 microliters of Matrigel was then placed over the specimens. The aortic segments were therefore embedded in the basement membrane matrix. Each well then received 300 microliters of MCDB 131 growth medium. The plates were placed in an incubator maintained at 37° C. with 5% $CO_2$. Specimens were observed daily over a 7 day period. Newly growing microvessels were counted using an inverted phase microscope at various times during the culture period, but data is expressed at 3 and 5 days of culture. To test for the effect of Type IV collagen on angiogenesis, domains at known concentrations were mixed with the Matrigel and with the MCDB 131 growth medium. Fresh MCDB 131 growth medium (plus and minus collagen domains) was changed every 3 days.

B. Results

Figure 2:
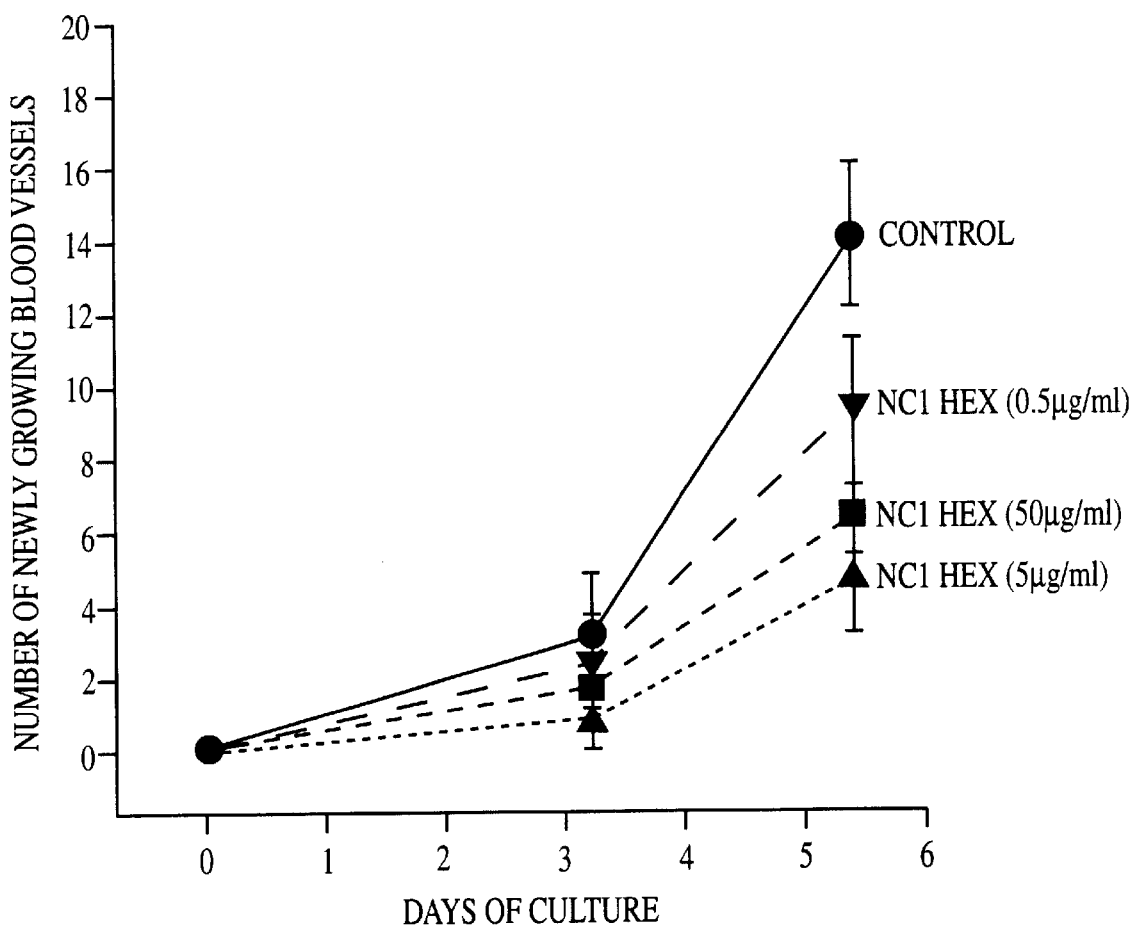
FIG. 2 illustrates the effects of 7S domain of Type IV collagen on angiogenesis from mouse thoracic aorta organ cultures. The domain concentrations employed in this experiment were 0 $\mu$g/ml (control); 0.5 $\mu$g/ml; 5 $\mu$g/ml and 50 $\mu$g/ml.
Figure 3:
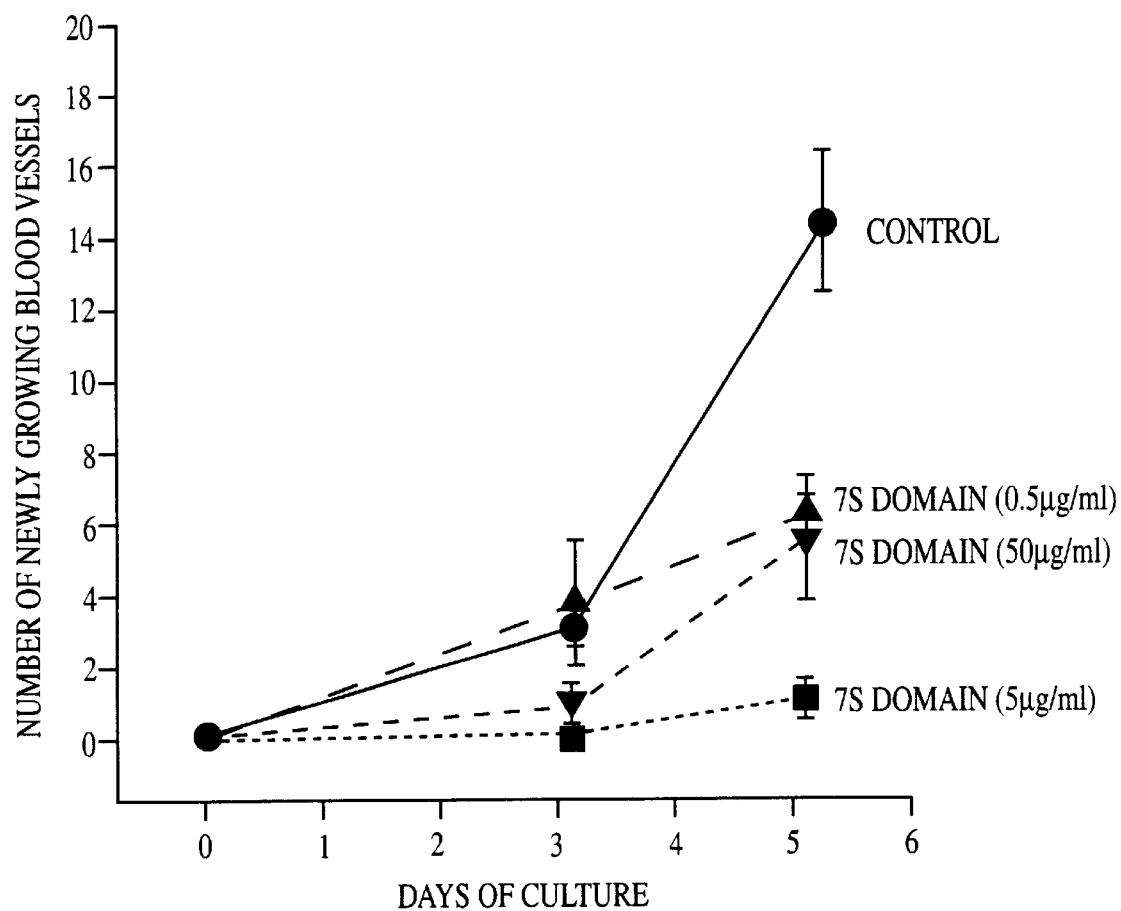
FIG. 3 illustrates the effects of NC1 (Hexamer) domain of Type IV collagen on angiogenesis from mouse thoracic aorta organ cultures. The domain concentrations employed in this experiment were 0 μg/ml (control); 5 μg/ml and 5 μg/ml and 50 μg/ml.

After establishing the time course of angiogenesis under control conditions (Matrigel plus MCDB 131 growth medium), experiments were performed using various concentrations of Type IV collagen (isolated from bovine lens) NC1 (hexamer) and 7S domains. Data represents the analysis of at least 3 specimens per experimental condition. In the first experiment (FIG. 1), analysis indicated that at a concentration of 50 μg/ml, NC1 domain and 7S domain significantly inhibited angiogenesis as monitored at 3 and 5 days of culture. In the second experiment, various concentrations of these domains were analyzed. As indicated in FIG. 3, 7S domain at 50 μg/ml again significantly inhibited angiogenesis at 3 and 5 days. Inhibition was reduced at 5 and 0.5 μg/ml concentrations. As indicated in FIG. 2, NC1 domain was less effective in blocking angiogenesis as compared to that observed in the first experiment (FIG. 1), although it was still effective. In addition, as compared to the 7S domain, there was less of a correlation between concentration and inhibitory action.

Figure 4A:
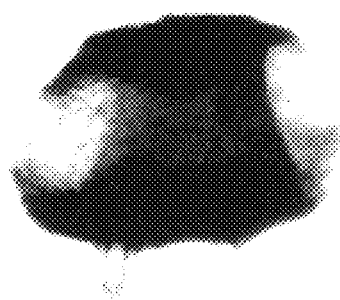
FIG. 4 are photographs of mouse thoracic aorta segments embedded in Matrigel (EHS basement membrane matrix, Collaborative Biomedical Products, Bedford, Mass.) at 5 days of culture. Control specimen (0 μg/ml of NC1 (Hexamer) and 7S domains) exhibited growth of microvessels from the cultured tissue into the matrix (FIG. 4A). In contrast, angiogenesis was inhibited in specimens cultured with 50 μg/ml of 7S domain (FIG. 4B) and NC1 (Hexamer) domain (FIG. 4C).
Figure 4B:
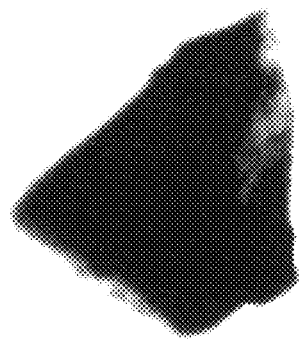
Figure 4C:
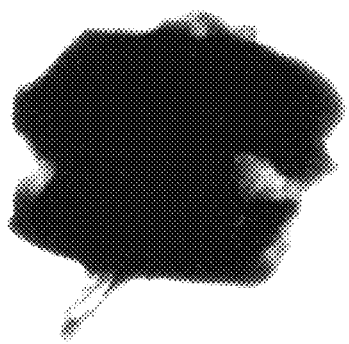

FIGS. 4A–C are photographs of mouse thoracic aorta segments embedded in Matrigel (EHS basement membrane matrix, Collaborative Biomedical Products, Bedford, Mass.) at 5 days of culture in the presence or absence of 50 μg/ml of Type IV collagen domains. The control specimen (no domains) exhibited growth of microvessels from the cultured tissue into the matrix (FIG. 4A). In contrast, angiogenesis inhibition was observed in tissues cultured in the presence of 50 μg/ml of 7S (FIG. 4B) and NC1 (Hexamer) domain (FIG. 4C).

EXAMPLE 2

Subcutaneous Fibrin Implant Angiogenesis

Recombinant human type IV collagen NC1 (α3) monomer (Sado et al., Kidney International 53:664–671 (1998))

was injected intravenously in Fisher 344 rats containing fibrin implants surgically placed subcutaneously, a modified version of the method described by Dvorak et al (Lab. Invest. 57(6):673–686 (1987)). The implants were then removed and directly analyzed using an inverted microscope. The analysis involved counting the number of blood vessels that had grown into the fibrin in the control and experimental group.

Briefly, 4 fibrin implants were surgically implanted subcutaneously into Fisher 344 rats (2 dorsal and 2 ventral sides). The average rat weight was approximately 125 grams.

Three rats (EXP) were given tail vein injections of either control (fibrin alone), 100 μl of 100 μg/ml of 7S domain of type IV collagen (approximately 0.80 mg/kg body weight), 100 μl of 100 μg/ml of type IV collagen hexamer (approximately 0.80 mg/kg body weight), or recombinant collagen type IV NC1 (α3) monomer at a concentration of 1.26 mg/ml in PBS (120 g protein, or approximately 0.96 mg/kg body weight) and 3 rats (C) were given 100 μl tail vein injections of PBS. Injections of recombinant protein were given every other day for five doses. The injection schedule was as follows:

Day 1: (implant day) injection and remove blood sample (EXP and C)

Day 3: Injection (EXP and C)

Day 5: Injection and remove blood sample (EXP and C)

Day 7: Injection (EXP and C)

Day 9: Injection and remove blood sample (EXP and C)

Day 11: Remove and fix implants (save blood sample) (EXP and C)

The results of one experiment were as follows:

| 2 week in vivo experiment: | |
| --- | --- |
| Control (fibrin alone) | about 66 BV |
| 7S domain of type IV lens collagen (100 μg/ml) | None |
| Hexamer of type IV lens collagen (100 μg/ml) | None |
| Monomer (α3) | None |

The results are shown as the mean number of blood vessels per implant. The results of this study demonstrate that isolated domains of type IV collagen, including the α3 monomer, can significantly inhibit capillary growth in the in vivo fibrin clot implant model. In subsequent experiments, the inhibitory effect was occasionally, seen to attenuate with time, suggesting that higher dosages or more frequent injections might be even more effective.

Figure 5:
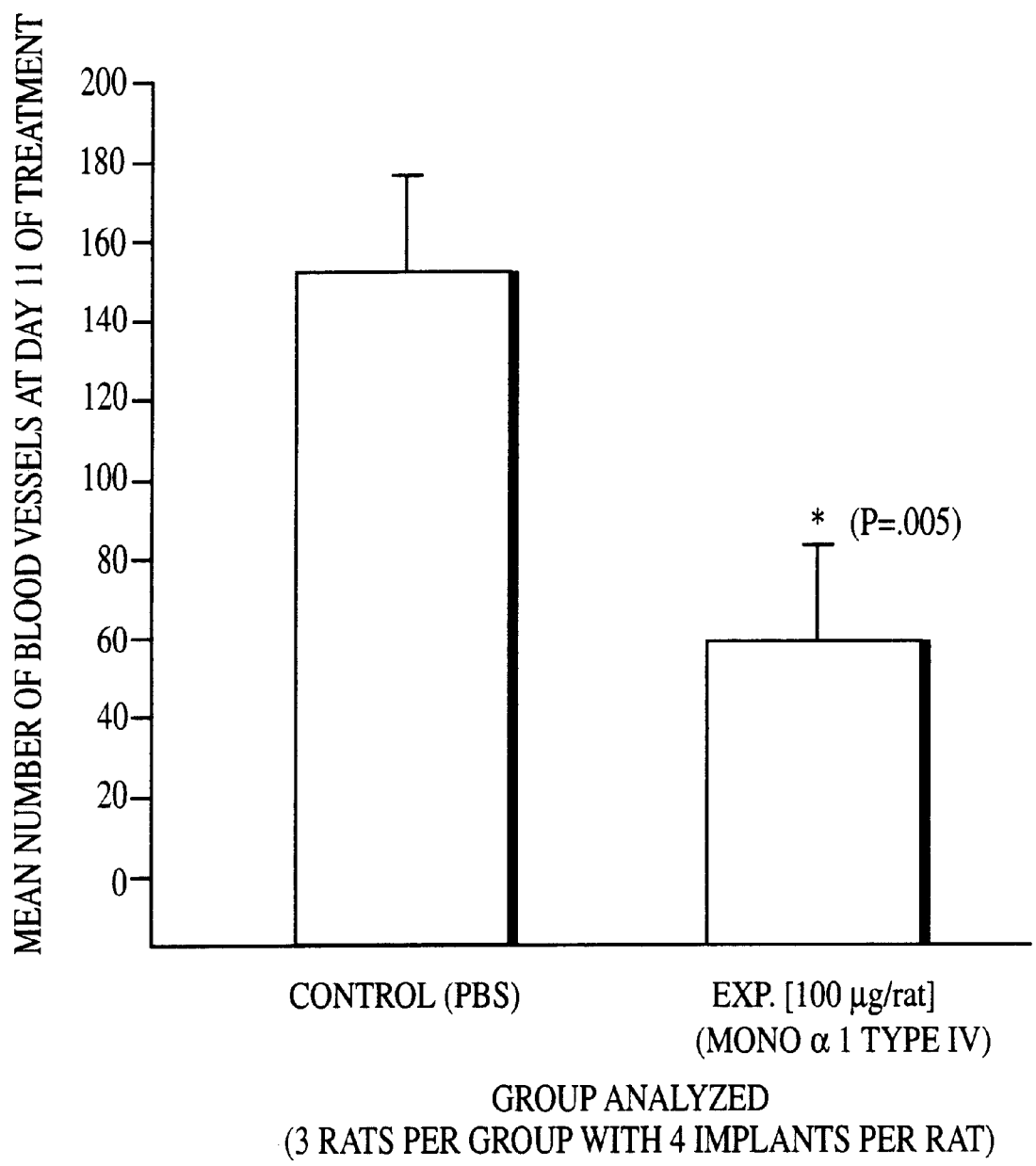
FIG. 5 is a graphical representation of data demonstrating the in vivo effect of IV injection of recombinant (α1) type IV collagen monomer on angiogenesis using fibrin implants in rats.
Figure 6:
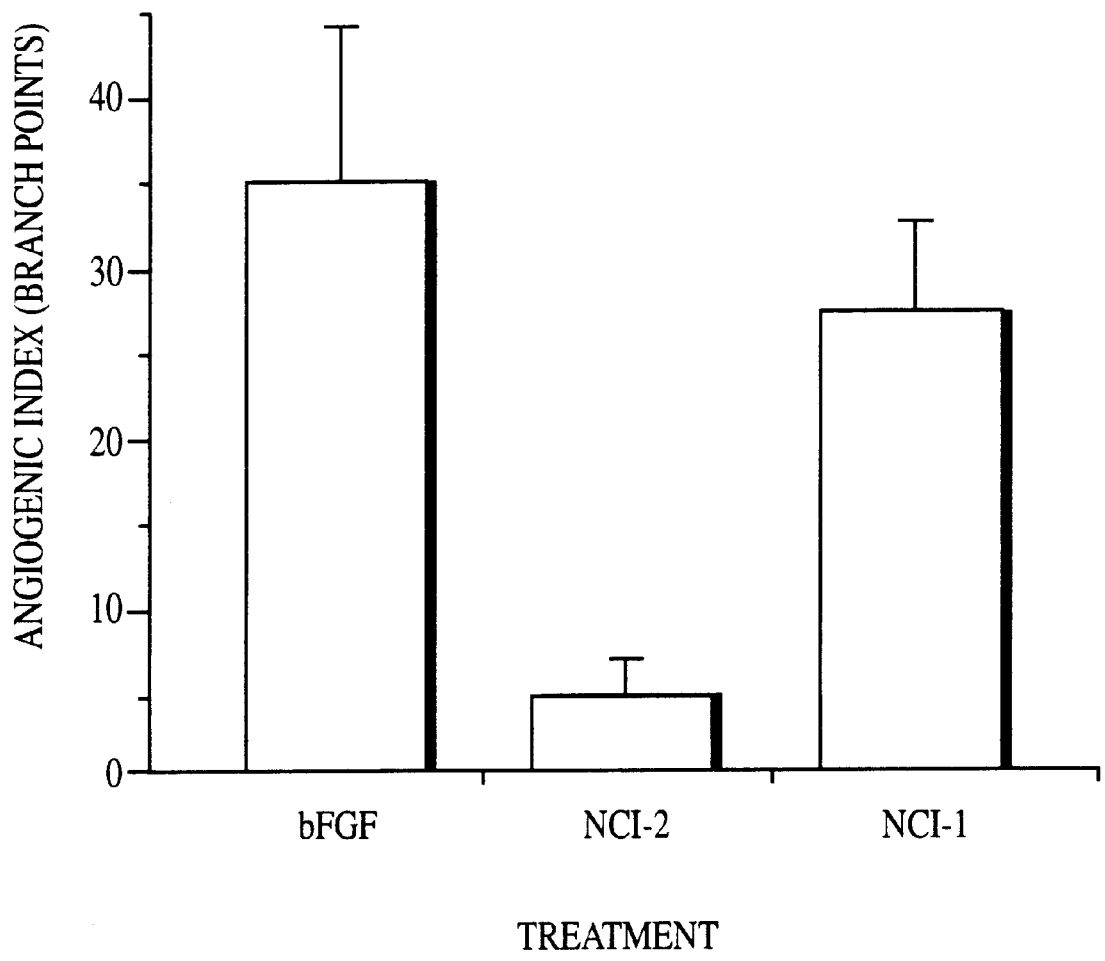
FIG. 6 is a graphical representation of data demonstrating that the recombinant (α1) and (α2) NC1 monomers inhibit the bFGF-induced increase in angiogenic index in vivo.
Figure 7:
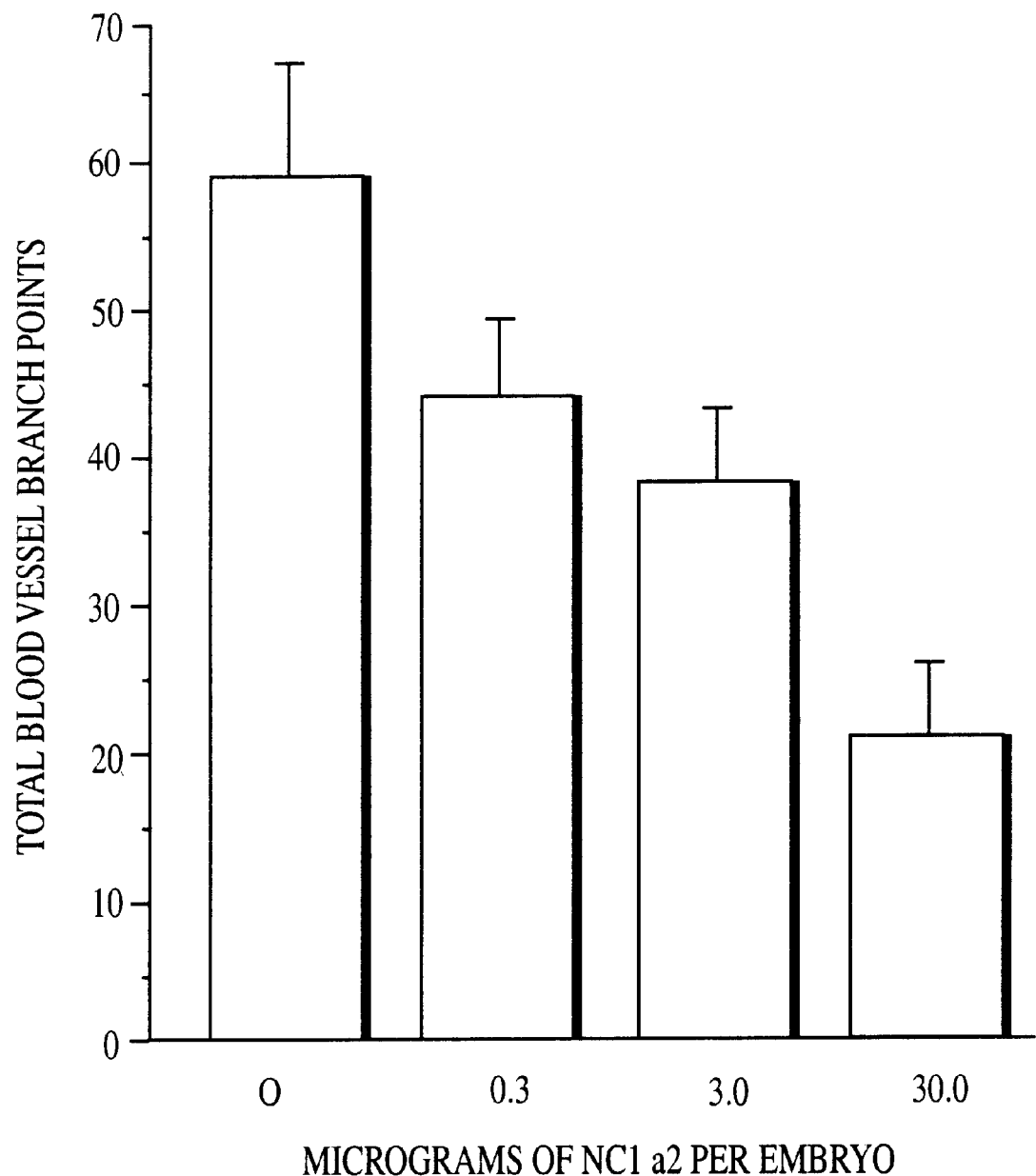
FIG. 7 is a graphical representation of demonstrating the dose response effect of recombinant (α2) NC1 monomer on the bFGF-induced increase in total blood vessel branch points in vivo.
Figure 8:
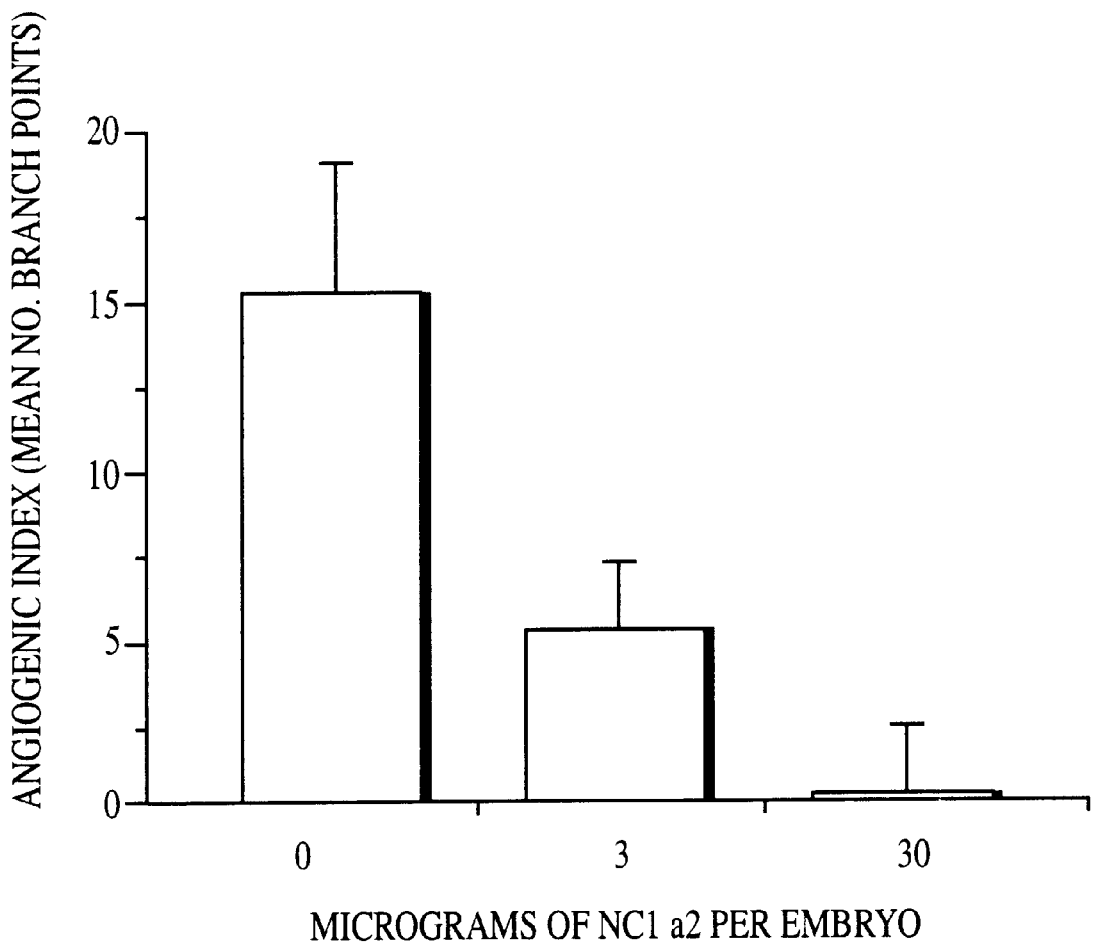
FIG. 8 is a graphical representation of data demonstrating the dose response effect of recombinant (α2) NC1 monomer on the bFGF-induced increase in angiogenic index in vivo.
Figure 9:
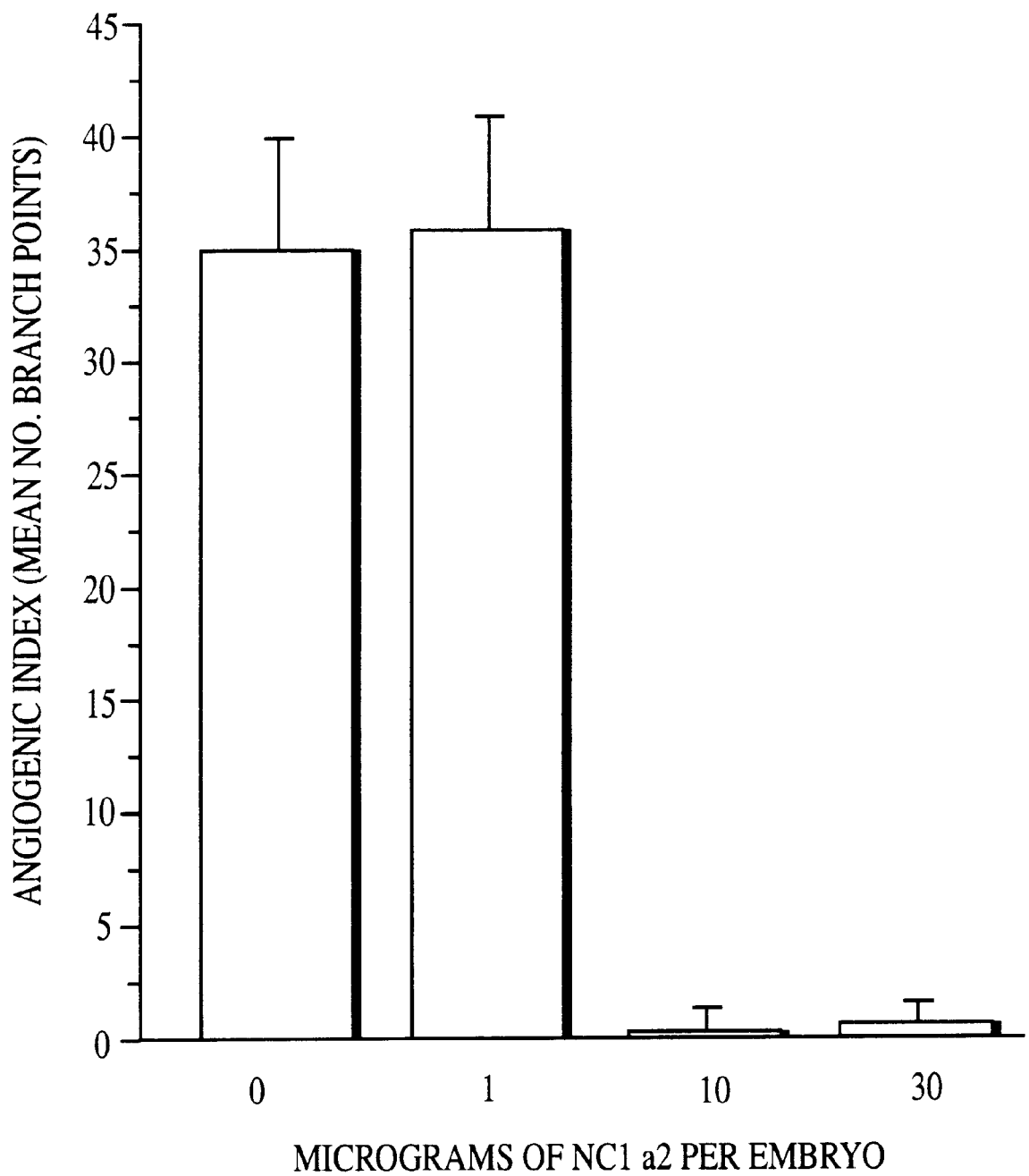
FIG. 9 is a graphical representation of data demonstrating the dose response effect of recombinant (α2) NC1 monomer on the bFGF-induced increase in angiogenic index in vivo.

A similar experiment was conducted using recombinant human type IV collagen NC1 (α1) monomer (100 μl of a 1 μg/μl solution; approximately 0.80 mg/kg body weight) and comparing the number of blood vessels that had grown into the fibrin at day 11 of treatment relative to the control group. Three rats per group were analyzed with each rat having 4 implants. These experiments demonstrated that administration of the al monomer significantly inhibited capillary growth in the in vivo fibrin clot implant model (FIG. 5).

EXAMPLE 3

Recombinant NC1 (α2) Domain Inhibits Angiogenesis in vivo

We next tested the effects of systemic administration of soluble NC1 α-chain monomers in the chick embryo CAM angiogenesis assay.

Angiogenesis was induced in the CAMs of 10 day old chick embryos with bFGF as described (Brooks et al., Cell 92:391–400 (1998)). Twenty four hours later the embryos were systemically treated with various concentrations of recombinant NC1 (α-chain monomers, in a total volume of 100 μl of sterile phosphate buffered saline (PBS). Two days later the embryos were sacrificed and the filter discs and CAM tissues removed. Angiogenesis was quantitated by counting the number of angiogenic blood vessel branch points in the confined area of the filter disc. The Angiogenic Index is defined as the number of branch points from experimental treatment minus control treatment.

In initial experiments, recombinant α1 or α2 NC1 domains were injected at a concentration of 50 μg per embryo. At this concentration, the NC1 domains were shown to be highly toxic as demonstrated by greater than 90% embryo cell death. However, at lower doses they were well tolerated and showed potent anti-angiogenic activity. A total of 6 individual angiogenesis experiments were conducted with the NC1 domains. However, in two experiments, the bFGF induction was low, making it difficult to interpret the results. The NC1 α2 domain appeared to be more consistent and potent than the α1 NC1 domain at inhibiting angiogenesis. In fact, systemic administration of 30 μg of NC1 α2 consistently inhibited angiogenesis by greater than 90% (FIGS. 6–9), as measured by inhibition of the bFGF-induced increase in the angiogenic index and the mean number of blood vessel branch points. In contrast, NC1 α1 domain showed variable inhibitory activity (0%–50%) throughout the experiments.

EXAMPLE 4

Recombinant NC1 Domain Inhibits Melanoma Tumor Growth in vivo

Since the growth of all solid tumors depends on angiogenesis to provide nutrients for its continued expansion, reagents that have the capacity to inhibit angiogenesis may significantly inhibit tumor growth. Therefore, we tested the effects of recombinant NC1 domains of type IV collagen for their effects on tumor growth in vivo.

Figure 10:
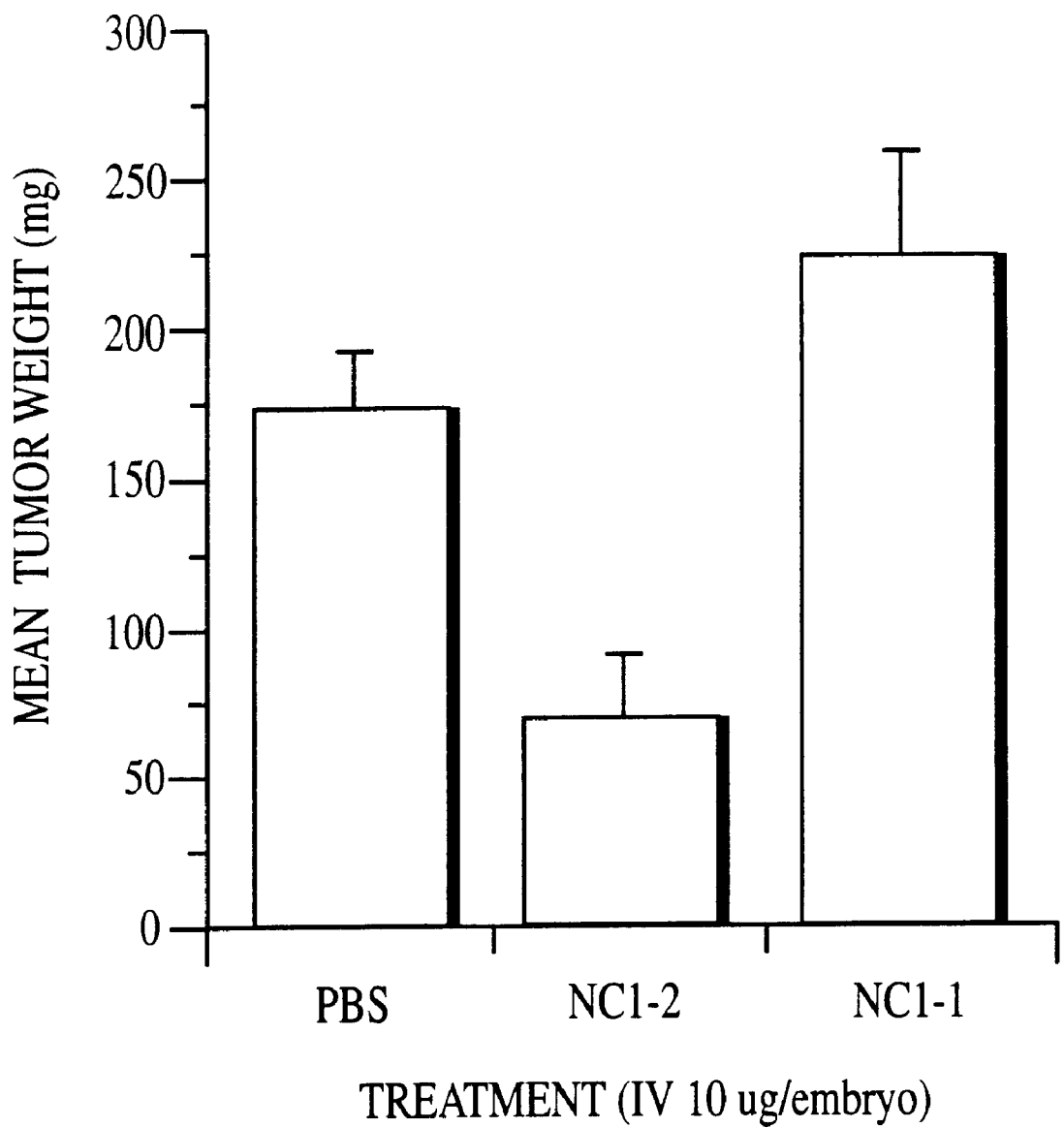
FIG. 10 is a graphical representation of data demonstrating the effect of recombinant (α1) and (α2) NC1 monomers on mean CS-1 melanoma tumor weight in vivo.
Figure 11:
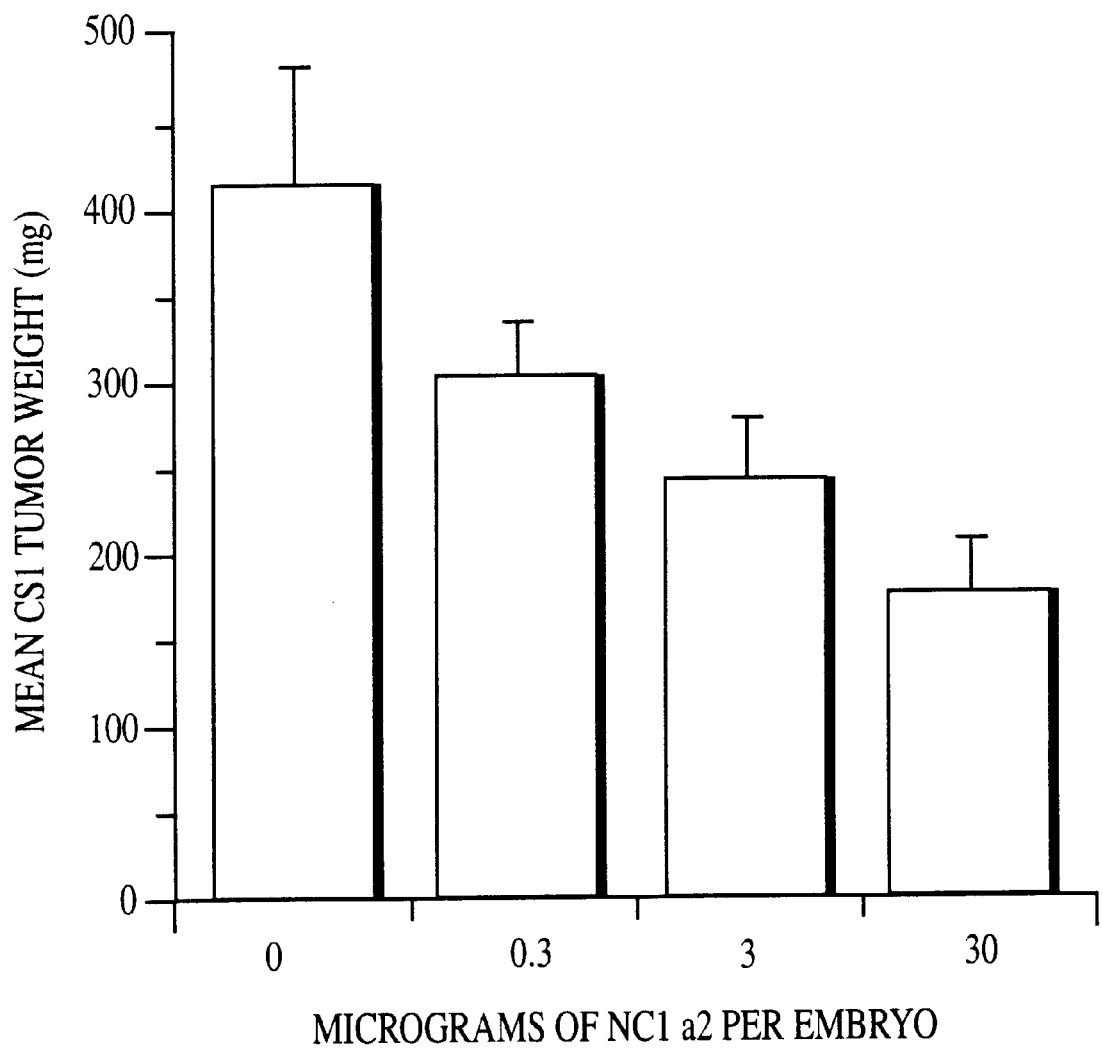
FIG. 11 is a graphical representation of data demonstrating the dose response effect of recombinant (α2) NC1 monomer on mean CS-1 melanoma tumor weight in vivo.
Figure 12:
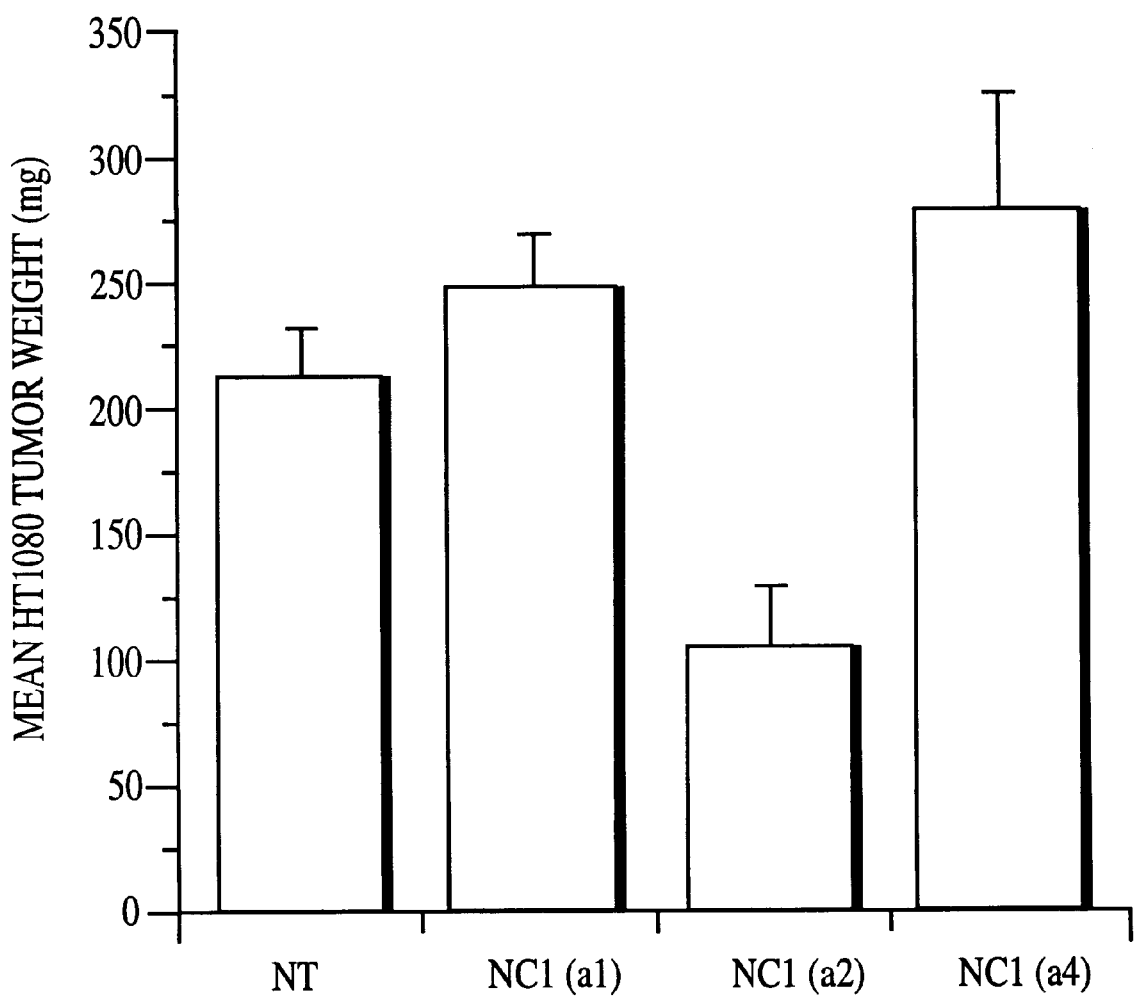
FIG. 12 is a graphical representation of data demonstrating the effect of recombinant (α1), (α2), and (α4) NC1 monomers on mean HT1080 tumor weight in vivo.
Figure 13:
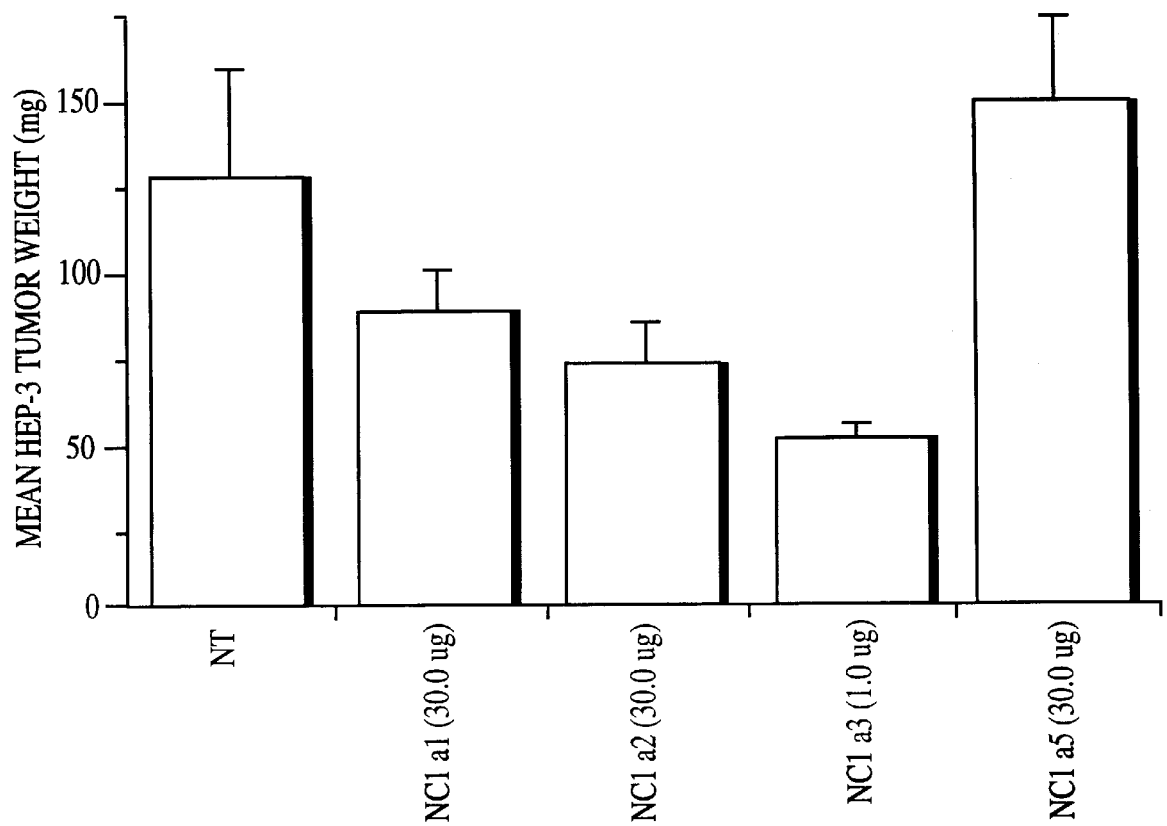
FIG. 13 is a graphical representation of data demonstrating the effect of recombinant (α1), (α2), (α3) and (α5) NC1 monomers on mean HEP-3 tumor weight in vivo.

To test the effects of NC1 domains on tumor growth in vivo, we utilized the chick embryo tumor growth assay. Briefly, single cell suspensions of 3 distinct tumor types were applied to the CAM of 10 day old chick embryos. The tumors included CS-1 Melanoma cells ($5\times10^6$), HT1080 human fibrosarcoma cells ($4\times10^5$) and Hep-3 human epidermoid carcinoma cells ($2\times10^5$). The embryos were injected systemically with varying concentrations of NC1 α-chain monomers 24 hours later. The embryos were next allowed to incubate for a total of 7 days, at which time they were sacrificed. The resulting tumors were resected and wet weights determined. A total of 6 tumor growth assays were conducted with the 3 distinct tumor types. A single injection of 10 μg NC1 α2 domain inhibited CS1 melanoma tumor growth by approximately 70% relative to control (FIG. 10). In similar experiments, dose response curves were completed with CS-1 tumors. Systemic administration of NC1 α2 resulted in a dose-dependent inhibition of CS-1 melanoma tumor growth in vivo with a maximum inhibition following a single dose at 30 μg (FIG. 11). Systemic administration of NC1 α1 also inhibited CS-1 tumor growth but it was variable and in some experiments failed to inhibit tumor growth (See FIG. 10). In similar experiments, NC1 α2 inhibited HT1080 human fibrosarcoma tumor growth by approximately 50% after a single systemic injection of 30 μg, while NC1 α1 and α4 had no effect (FIG. 12). Finally, systemic administration of NC1 α2 (30.0 μg) and α3 inhibited Hep-3 human epidermoid carcinoma tumor growth by approximately 40% and 60% respectively, and α1 inhibited Hep-3 tumor growth by approximately 30%, while NC1 α5 domain failed to inhibit tumor growth (FIG. 13).

We conclude from these in vivo studies that tumor growth can be inhibited by isolated NC1 α-chain monomers. These molecules can thus be used alone, or to complement the use of existing anti-tumor agents, in providing enhanced and more effective anti-tumor therapy.

EXAMPLE 5

Immobilized NC1 Domains Support Human Endothelial Cell Adhesion

In order for new blood vessels to form, endothelial cells must have the capacity to adhere and migrate through the ECM. Moreover, this endothelial cell-ECM interaction may facilitate signal transduction events required for-new blood vessel formation. Therefore, since type IV-collagen is an ECM protein which is known to support cell adhesion, we tested the ability of the NC1 domains to support endothelial cell attachment.

Microtiter plates were coated with 25 μg/ml of purified NC1 domains followed by incubation with 1% bovine serum albumin (BSA) to block non-specific interactions. Human endothelial cells (ECV304) were then allowed to attach to the immobilized NC1 domains for 1 hour. Non-adherent cells were removed by washing and attached cells were quantified by measuring the optical density (O.D.) of crystal violet eluted from attached cells. Data bars represent the mean +/− standard error of the O.D. from triplicate wells.

Figure 14:
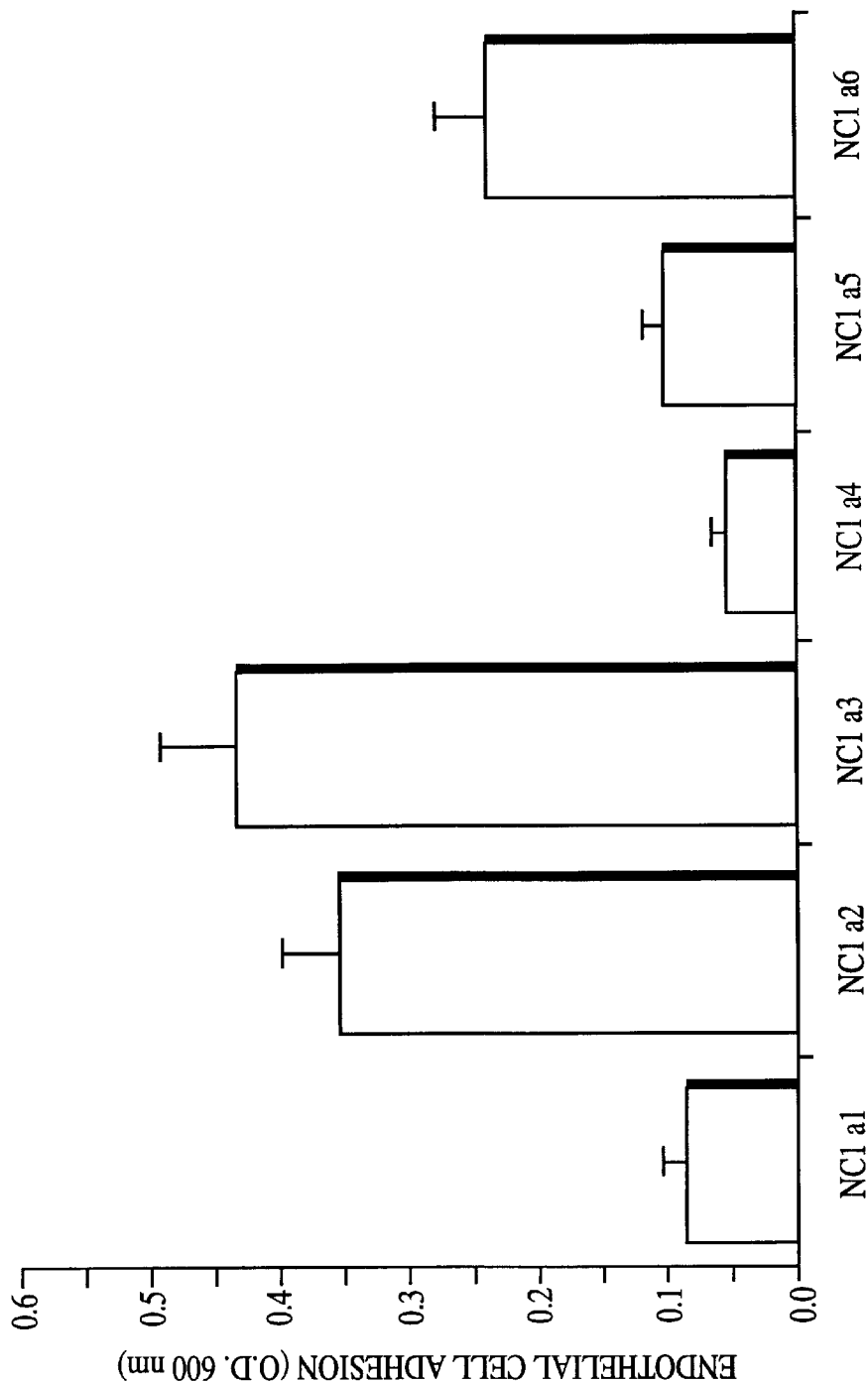
FIG. 14 is a graphical representation of data demonstrating human endothelial cell adhesion to immobilized NC1 α monomers.
Figure 15:
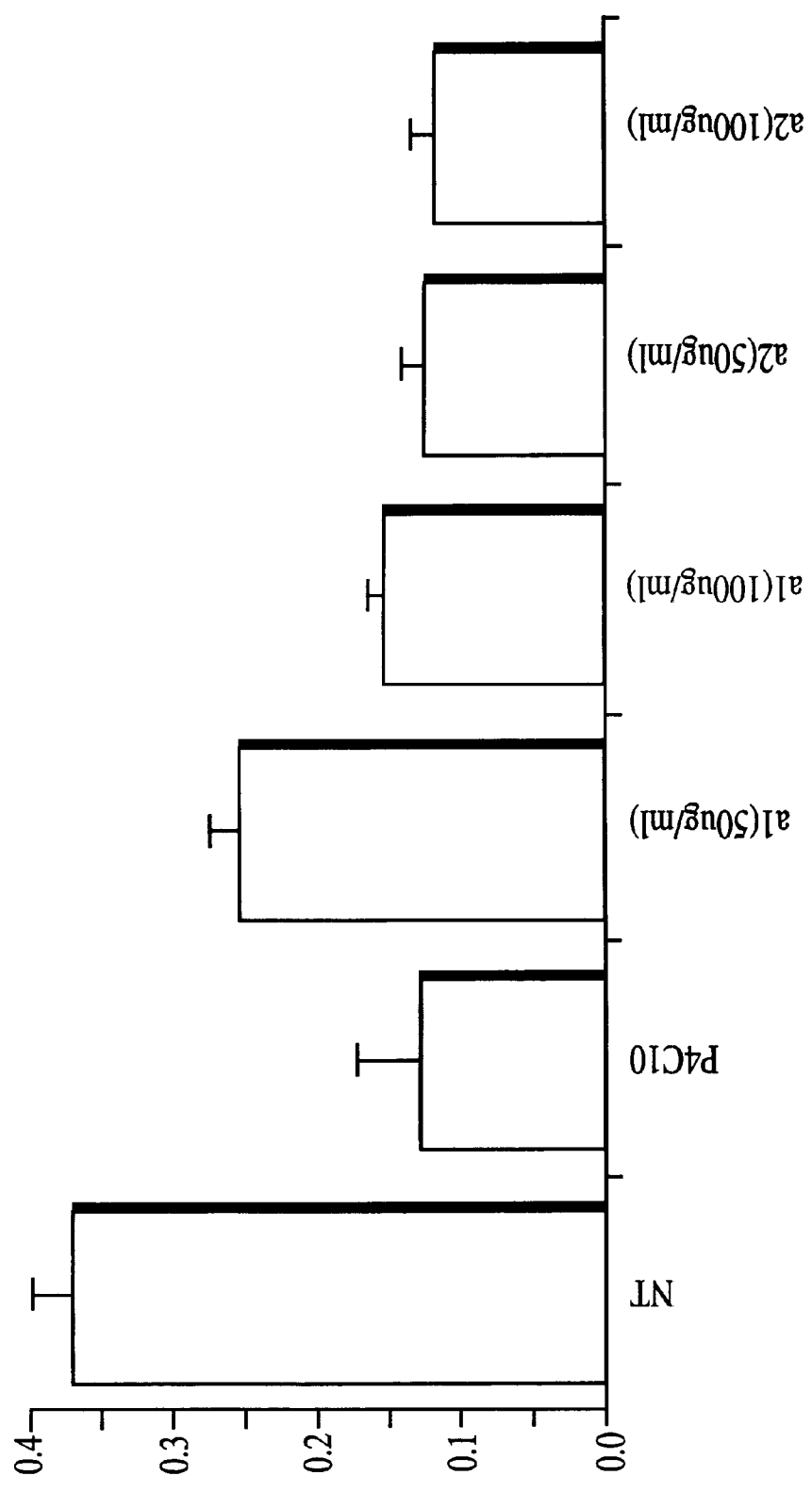
FIG. 15 is a graphical representation of data demonstrating the effect of soluble α1 and α2 NC1 monomers on human endothelial cell adhesion to pepsinized collagen type IV.

Immobilized NC1 α2, α3, and α6 domains supported endothelial cell adhesion while NC1 α1, α4, and α5 domains promoted little if any cell adhesion (FIG. 14). Soluble NC1 α1 (a1) and α2 (a2) inhibited endothelial cell adhesion to pepsinized collagen type IV by approximately 50% (FIG. 15).

Taken together, these findings demonstrate that isolated, recombinant NC1 domains from the α1, α2, α3, and α6 chains of collagen type IV can mediate human endothelial cell adhesion and/or inhibit endothelial cell adhesion to ECM proteins in vitro, and suggest that the potent anti-angiogenic and anti-tumor activity of the isolated NC1 domains is due to disruption of endothelial cell interaction with the extracellular matrix that are necessary for angiogenesis.

EXAMPLE 6

Endothelial Cell Migration

Invasive cellular processes such as angiogenesis and tumor metastasis also require cellular motility. Thus we evaluated the ability of isolated NC1 domains to support human endothelial cell migration in vitro. These experiments were conducted essentially according to the methods in Brooks et al., J. Clin. Invest. 99:1390–1398 (1997).

Figure 16:
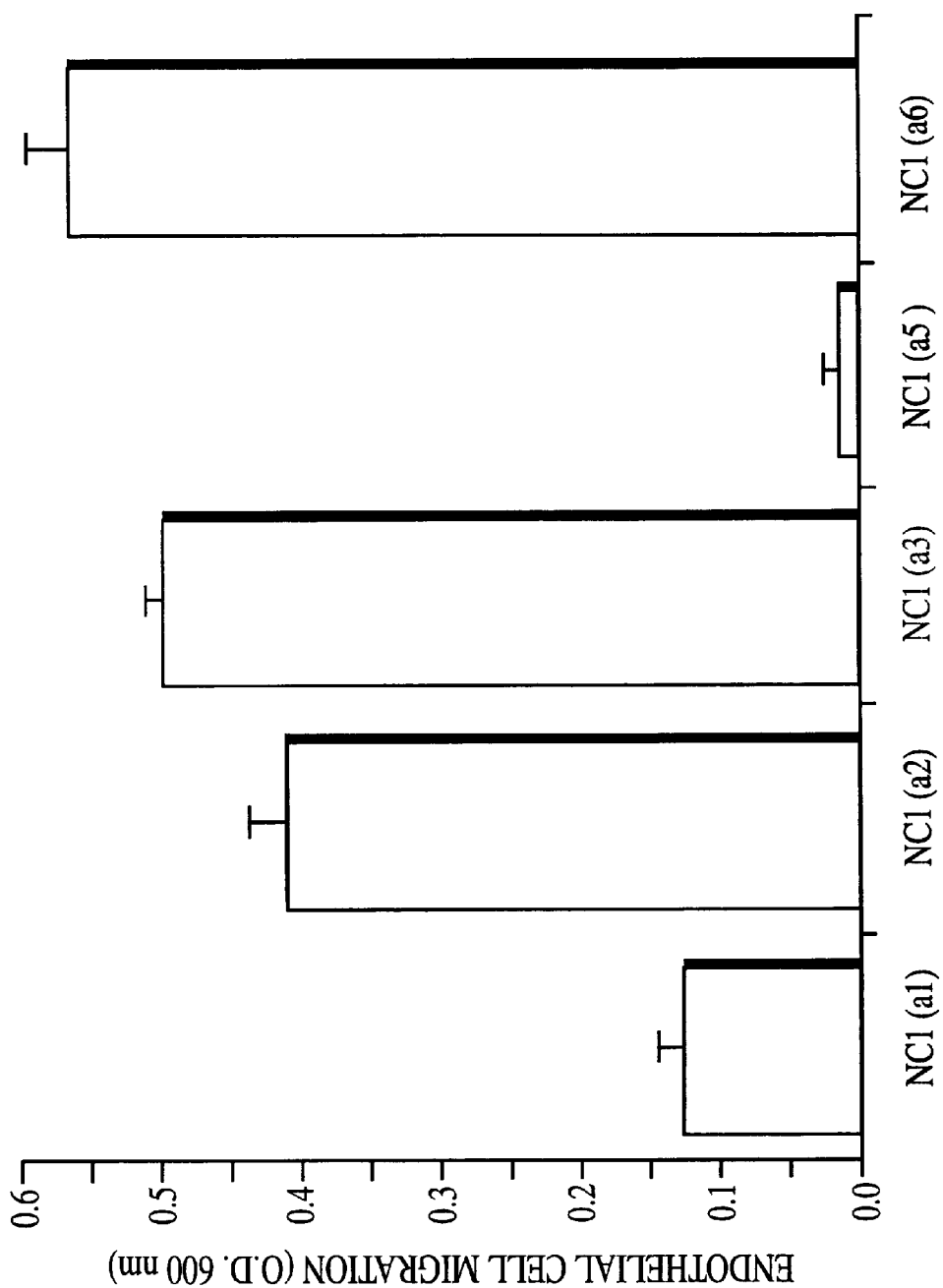
FIG. 16 is a graphical representation of data demonstrating the effect of isolated recombinant NC1 monomers on human endothelial cell migration in vitro.

The results of these experiments indicate that NC1 α2, α3, and α6 domains can support human endothelial cell migration in vitro, while α1, α4, and α5 domains showed little if any capacity to support endothelial cell migration (FIG. 16).

EXAMPLE 7

Efficacy in Lewis Lung in vivo Tumor

The above studies indicated that specific domains of collagen type IV can promote cell migration in vitro. Thus, we evaluated the ability of NC1 domains to support endothelial cell migration in vivo.

The α (IV) NC1 domain hexamer, isolated by enzymatic digestion of bovine lens capsule basement membrane by known protocols (Peczon et al., Exp. Eye Res. 30:155–165 (1980)) was tested in the metastatic Lewis lung mouse tumor model using a standard protocol which is considered to be a good model of both metastasis and angiogenesis of lung tumors. (See for example, Teicher et al., Anticancer Res. 18:2567–2573 (1998); Guibaud et al., Anticancer Drugs 8:276–282 (1997); Anderson et al., Cancer Res. 56:715–718 (1996)).

Each study consisted of an untreated control group and six treatment groups. There were ten animals per treatment group with 40 mice in the control. In each study, all treatment was administered intravenously once every 2 days for 7 doses starting one day after tumor inoculation. Dosages of α (IV) NC1 hexamer were either 100 μg/mouse or 200 μg/mouse. In the Lewis lung study, the tumor cell inoculum was $1 \times 10^6$ viable cells. All animals were weighed twice a week throughout the study. Starting one day after the last treatment, 5 mice were periodically sacrificed from each control group to measure pulmonary tumor burden. The experiment was terminated at day 14 when the lungs of the control animals had sufficient tumor mass to provide meaningful evaluation. At that time, the lungs of all remaining animals were excised, weighed, and the number of tumor foci greater than 2 mm in diameter counted. The resulting data showed that both dosages of α (IV) NC1 hexamer significantly reduced the number of visible lung metastases (Mann-Whitney Rank Sum Test, $p<0.05$), with 8 visible lung metastases in the control, vs. 5 (100 μg/mouse) and 4 (200 μg/mouse), and the 100 μg/mouse dosage reduced the lung weights from a median of 520 mg in controls to a median of 462 mg in experimental, while the median lung weight of mice treated with 200 μg/mouse was 620 mg.

Other in vivo studies demonstrated that tumor cell metastasis to the lung can be reduced by 50% or more using intravenous injections of the Type IV collagen domains in murine B16 melanoma, human A375SM melanoma xenografts. Furthermore, injection of the NC1 hexamer also significantly reduced the number of lung tumors in separate Lewis Lung tumor studies.

We conclude from all of the above studies that angiogenesis, tumor growth and metastasis, and endothelial cell adhesion to the ECM, can be inhibited by isolated, recombinant domains of type IV collagen. The present invention is thus broadly applicable to a variety of uses which include inhibition of angiogenesis and treatment of diseases and conditions with accompanying undesired angiogenesis, such as solid and blood-borne tumors including but not limited to melanomas, carcinomas, sarcomas, rhabdomyosarcoma, retinoblastoma., Ewing sarcoma, neuroblastoma, osteosarcoma, and leukemia.

The invention is further applicable to treating non-tumorigenic diseases and conditions with accompanying undesired angiogenesis, including but not limited to diabetic retinopathy, rheumatoid arthritis, retinal neovascularization, choroidal neovascularization, macular degeneration., corneal neovascularization, retinopathy of prematurity., corneal graft rejection, neovascular glaucoma., retrolental fibroplasia, epidemic keratoconjunctivitis, Vitamin A deficiency, contact lens overwear, atopic keratitis, superior limbic keratitis, pterygium keratitis sicca, sogrens, acne rosacea, phylectenulosis, syphilis, Mycobacteria infections, lipid degeneration, chemical burns, bacterial ulcers, fungal ulcers, Herpes simplex infections, Herpes zoster infections, protozoan infections, Kaposi's sarcoma, Mooren ulcer, Terrien's marginal degeneration, marginal keratolysis, traum, systemic lupus, polyarteritis, Wegeners sarcoidosis, scleritis, Steven's Johnson disease, radial keratotomy, sickle cell anemia, sarcoid, pseudoxanthoma elasticum, Pagets disease, vein occlusion, artery occulsion, carotid obstructive disease, chronic uveitis, chronic vitritis, Lyme's disease, Eales disease, Bechets disease, myopia, optic pits, Stargarts disease, pars planitis, chronic retinal detachment, hyperviscosity syndromes, toxoplasmosis, post-laser complications, abnormal proliferation of fibrovascular tissue, hemangiomas, Osler-Weber-Rendu, acquired immune deficiency syndrome, ocular neovascular disease, osteoarthritis, chronic inflammation, Crohn's disease, ulceritive colitis, psoriasis., atherosclerosis, and pemphigoid. See U.S. Pat. No. 5,712,291)

The invention is also broadly applicable to methods for inhibiting tumor growth and metastasis, reduction of scar tissue formation, reduction of complications due to cell adhesion in organ transplants, and the inhibition of lymphocyte adhesion and mobility.

While the fundamental novel features of the invention have been shown and described, it will be understood that various omissions, substitutions, and changes in the form and details illustrated may be made by those skilled in the art without departing from the spirit of the invention. For example, various modifications, additions. and/or substitutions can be made to the type IV collagen a monomer chains that would be encompassed by the invention. It is the intention, therefore, to be limited only as indicated by the scope of the following claims:

We claim:

1. A pharmaceutical composition consisting of:
   a) an amount effective of isolated NC1 $\alpha 2$ chain monomers of type IV collagen to inhibit angiogenesis, tumor metastasis, or tumor growth in a host in need thereof, or to treat an angiogenesis-mediated disease or condition in a mammal; and
   b) a pharmaceutically acceptable carrier.

2. The pharmaceutical composition of claim 1 wherein the NC1 $\alpha 2$ chain domain is present at a concentration permitting administration to a subject in need thereof at a dosage of at least 0.01 microgram per kilogram body weight of the subject.

3. The pharmaceutical composition of claim 1 wherein the NC1 $\alpha 2$ chain domain is present at a concentration permitting administration to a subject in need thereof at a dosage of between 0.01 microgram per kilogram body weight of the subject and 10 milligrams per kilogram body weight of the subject.

4. The pharmaceutical composition of claim 1 wherein the NC1 $\alpha 2$ chain domain is present at a concentration permitting administration to a subject in need thereof at a dosage of between 0.05 microgram per kilogram body weight of the subject and 5 milligrams per kilogram body weight of the subject.

\* \* \* \* \*